(12) United States Patent
Park et al.

(10) Patent No.: US 8,801,719 B2
(45) Date of Patent: Aug. 12, 2014

(54) TOTAL JOINT ARTHROPLASTY SYSTEM

(71) Applicant: OtisMed Corporation, Alameda, CA (US)

(72) Inventors: Ilwhan Park, Walnut Creek, CA (US); Lacerial Pearson, Livermore, CA (US); Stephen M. Samuel, San Jose, CA (US)

(73) Assignee: OtisMed Corporation, Alameda, CA (US)

( * ) Notice: Subject to any disclaimer, the term of this patent is extended or adjusted under 35 U.S.C. 154(b) by 0 days.

(21) Appl. No.: 13/730,585

(22) Filed: Dec. 28, 2012

(65) Prior Publication Data

US 2013/0190767 A1    Jul. 25, 2013

Related U.S. Application Data

(63) Continuation of application No. 11/641,569, filed on Dec. 18, 2006, which is a continuation of application No. 10/146,862, filed on May 15, 2002, now abandoned.

(51) Int. Cl.
| | |
|---|---|
| *A61F 2/46* | (2006.01) |
| *A61F 5/00* | (2006.01) |
| *A61B 17/58* | (2006.01) |
| *A61B 17/60* | (2006.01) |
| *A61F 2/00* | (2006.01) |

(52) U.S. Cl.
USPC .............................. 606/87; 606/86 R; 606/88

(58) Field of Classification Search
USPC .......................................... 606/88, 86 R, 87
See application file for complete search history.

(56) References Cited

U.S. PATENT DOCUMENTS

| | | |
|---|---|---|
| 3,195,411 A | 7/1965 | MacDonald et al. |
| 3,825,151 A | 7/1974 | Arnaud |

(Continued)

FOREIGN PATENT DOCUMENTS

| | | |
|---|---|---|
| DE | 3305237 A1 | 8/1983 |
| DE | 4341367 C1 | 6/1995 |

(Continued)

OTHER PUBLICATIONS

Advisory Action and Interview Summary, U.S. Appl. No. 12/390,667, mailed Apr. 27, 2012, 23 pages.

(Continued)

*Primary Examiner* — David Bates
(74) *Attorney, Agent, or Firm* — Polsinelli PC

(57) ABSTRACT

A method and system for performing a total joint arthroplasty procedure on a patient's damaged bone region. A CT image or other suitable image is formed of the damaged bone surfaces, and location coordinate values $(x_n, y_n, z_n)$ are determined for a selected sequence of bone surface locations using the CT image data. A mathematical model $z = f(x,y)$ of a surface that accurately matches the bone surface coordinates at the selected bone spice locations, or matches surface normal vector components at selected bone surface locations, is determined. The model provides a production file from which a cutting jig and an implant device (optional), each patient-specific and having controllable alignment, are fabricated for the damaged bone by automated processing. At this point, the patient is cut open (once), the cutting jig and a cutting instrument are used to remove a selected portion of the bone and to provide an exposed planar surface, the implant device is optionally secured to and aligned with the remainder of the bone, and the patient's incision is promptly repaired.

25 Claims, 10 Drawing Sheets

(56) References Cited

U.S. PATENT DOCUMENTS

| | | |
|---|---|---|
| D245,920 S | 9/1977 | Shen |
| 4,198,712 A | 4/1980 | Swanson |
| 4,298,992 A | 11/1981 | Burstein |
| 4,436,684 A | 3/1984 | White |
| D274,093 S | 5/1984 | Kenna |
| D274,161 S | 6/1984 | Kenna |
| 4,467,801 A | 8/1984 | Whiteside |
| 4,575,330 A | 3/1986 | Hull |
| 4,646,726 A | 3/1987 | Westin et al. |
| 4,719,585 A | 1/1988 | Cline et al. |
| 4,721,104 A | 1/1988 | Kaufman et al. |
| 4,821,213 A | 4/1989 | Cline et al. |
| 4,822,365 A | 4/1989 | Walker et al. |
| 4,825,857 A | 5/1989 | Kenna |
| 4,841,975 A | 6/1989 | Woolson |
| 4,931,056 A | 6/1990 | Ghajar et al. |
| 4,936,862 A | 6/1990 | Walker et al. |
| 4,976,737 A | 12/1990 | Leake |
| 5,007,936 A | 4/1991 | Woolson |
| 5,011,405 A | 4/1991 | Lemchen |
| 5,027,281 A | 6/1991 | Rekow et al. |
| 5,030,219 A | 7/1991 | Matsen, III et al. |
| 5,037,424 A | 8/1991 | Aboczsky |
| 5,075,866 A | 12/1991 | Goto et al. |
| 5,078,719 A | 1/1992 | Schreiber |
| 5,086,401 A | 2/1992 | Glassman et al. |
| 5,098,383 A | 3/1992 | Hemmy et al. |
| 5,099,846 A | 3/1992 | Hardy |
| 5,122,144 A | 6/1992 | Bert et al. |
| 5,123,927 A | 6/1992 | Duncan et al. |
| 5,139,419 A | 8/1992 | Andreiko et al. |
| 5,140,646 A | 8/1992 | Ueda |
| 5,141,512 A | 8/1992 | Farmer et al. |
| 5,154,717 A | 10/1992 | Matsen, III et al. |
| 5,156,777 A | 10/1992 | Kaye |
| 5,171,276 A | 12/1992 | Caspari et al. |
| D336,518 S | 6/1993 | Taylor |
| 5,218,427 A | 6/1993 | Koch |
| 5,234,433 A | 8/1993 | Bert et al. |
| 5,236,461 A | 8/1993 | Forte |
| 5,274,565 A | 12/1993 | Reuben |
| 5,298,115 A | 3/1994 | Leonard |
| 5,298,254 A | 3/1994 | Prewett et al. |
| 5,305,203 A | 4/1994 | Raab |
| D346,979 S | 5/1994 | Stalcup et al. |
| 5,320,529 A | 6/1994 | Pompa |
| 5,360,446 A | 11/1994 | Kennedy |
| 5,364,402 A | 11/1994 | Mumme et al. |
| 5,365,996 A | 11/1994 | Crook |
| 5,368,478 A | 11/1994 | Andreiko et al. |
| D355,254 S | 2/1995 | Krafft et al. |
| D357,315 S | 4/1995 | Dietz |
| 5,408,409 A | 4/1995 | Glassman et al. |
| 5,431,562 A | 7/1995 | Andreiko et al. |
| 5,448,489 A | 9/1995 | Reuben |
| 5,452,407 A | 9/1995 | Crook |
| 5,462,550 A | 10/1995 | Dietz et al. |
| 5,484,446 A | 1/1996 | Burke et al. |
| D372,309 S | 7/1996 | Heldreth |
| D374,078 S | 9/1996 | Johnson et al. |
| 5,556,278 A | 9/1996 | Meitner |
| 5,569,260 A | 10/1996 | Petersen |
| 5,569,261 A | 10/1996 | Marik et al. |
| 5,601,563 A | 2/1997 | Burke et al. |
| 5,601,565 A | 2/1997 | Huebner |
| 5,662,656 A | 9/1997 | White |
| 5,681,354 A | 10/1997 | Eckhoff |
| 5,682,886 A | 11/1997 | Delp et al. |
| 5,683,398 A | 11/1997 | Carls et al. |
| 5,690,635 A | 11/1997 | Matsen, III et al. |
| 5,716,361 A | 2/1998 | Masini |
| 5,725,376 A | 3/1998 | Poirier |
| 5,735,277 A | 4/1998 | Schuster |
| 5,741,215 A | 4/1998 | D'Urso |
| 5,749,876 A | 5/1998 | Duvillier et al. |
| 5,768,134 A | 6/1998 | Swaelens et al. |
| 5,769,092 A | 6/1998 | Williamson, Jr. |
| 5,769,859 A | 6/1998 | Dorsey |
| D398,058 S | 9/1998 | Collier |
| 5,810,830 A | 9/1998 | Noble et al. |
| 5,824,085 A | 10/1998 | Sahay et al. |
| 5,824,098 A | 10/1998 | Stein |
| 5,824,100 A | 10/1998 | Kester et al. |
| 5,824,111 A | 10/1998 | Schall et al. |
| 5,860,980 A | 1/1999 | Axelson, Jr. et al. |
| 5,860,981 A | 1/1999 | Bertin et al. |
| 5,871,018 A | 2/1999 | Delp et al. |
| 5,880,976 A | 3/1999 | DiGioia, III et al. |
| 5,908,424 A | 6/1999 | Bertin et al. |
| 5,911,724 A | 6/1999 | Wehrli |
| 5,916,221 A | 6/1999 | Hodorek et al. |
| 5,964,808 A | 10/1999 | Blaha et al. |
| 5,967,777 A | 10/1999 | Klein et al. |
| 5,993,448 A | 11/1999 | Remmler |
| 5,995,738 A | 11/1999 | DiGioia, III et al. |
| 6,002,859 A | 12/1999 | DiGioia, III et al. |
| 6,068,658 A | 5/2000 | Insall et al. |
| 6,090,114 A | 7/2000 | Matsuno et al. |
| 6,096,043 A | 8/2000 | Techiera et al. |
| 6,106,529 A | 8/2000 | Techiera |
| 6,112,109 A | 8/2000 | D'Urso |
| 6,126,690 A | 10/2000 | Ateshian et al. |
| 6,132,447 A | 10/2000 | Dorsey |
| 6,161,080 A | 12/2000 | Aouni-Ateshian et al. |
| 6,171,340 B1 | 1/2001 | McDowell |
| 6,173,200 B1 | 1/2001 | Cooke et al. |
| 6,183,515 B1 | 2/2001 | Barlow et al. |
| 6,205,411 B1 | 3/2001 | DiGioia, III et al. |
| 6,228,121 B1 | 5/2001 | Khalili |
| 6,254,639 B1 | 7/2001 | Peckitt |
| 6,285,902 B1 | 9/2001 | Kienzle, III et al. |
| 6,327,491 B1 | 12/2001 | Franklin et al. |
| 6,343,987 B2 * | 2/2002 | Hayama et al. ............... 463/1 |
| 6,382,975 B1 | 5/2002 | Poirier |
| 6,383,228 B1 * | 5/2002 | Schmotzer ............ 623/23.35 |
| 6,385,475 B1 | 5/2002 | Cinquin et al. |
| 6,415,171 B1 | 7/2002 | Gueziec et al. |
| 6,458,135 B1 | 10/2002 | Harwin et al. |
| 6,463,351 B1 | 10/2002 | Clynch |
| 6,503,254 B2 | 1/2003 | Masini |
| 6,510,334 B1 | 1/2003 | Schuster et al. |
| 6,514,259 B2 | 2/2003 | Picard et al. |
| 6,520,964 B2 | 2/2003 | Tallarida et al. |
| 6,533,737 B1 | 3/2003 | Brosseau et al. |
| D473,307 S | 4/2003 | Cooke |
| 6,540,784 B2 | 4/2003 | Barlow et al. |
| 6,558,426 B1 | 5/2003 | Masini |
| 6,575,980 B1 | 6/2003 | Robie et al. |
| 6,602,259 B1 | 8/2003 | Masini |
| 6,672,870 B2 | 1/2004 | Knapp |
| 6,692,448 B2 | 2/2004 | Tanaka et al. |
| 6,701,174 B1 | 3/2004 | Krause et al. |
| 6,702,821 B2 | 3/2004 | Bonutti |
| 6,711,431 B2 | 3/2004 | Sarin et al. |
| 6,711,432 B1 | 3/2004 | Krause et al. |
| 6,712,856 B1 | 3/2004 | Carignan et al. |
| 6,716,249 B2 * | 4/2004 | Hyde ..................... 623/21.16 |
| 6,738,657 B1 | 5/2004 | Franklin et al. |
| 6,747,646 B2 | 6/2004 | Gueziec et al. |
| 6,770,099 B2 | 8/2004 | Andriacchi et al. |
| 6,772,026 B2 | 8/2004 | Bradbury et al. |
| 6,799,066 B2 | 9/2004 | Steines et al. |
| 6,814,575 B2 | 11/2004 | Poirier |
| 6,905,510 B2 | 6/2005 | Saab |
| 6,905,514 B2 | 6/2005 | Carignan et al. |
| 6,923,817 B2 | 8/2005 | Carson et al. |
| 6,932,842 B1 | 8/2005 | Litschko et al. |
| 6,944,518 B2 | 9/2005 | Roose |
| 6,955,345 B2 | 10/2005 | Kato |
| 6,969,393 B2 | 11/2005 | Pinczewski et al. |
| 6,975,894 B2 | 12/2005 | Wehrli et al. |
| 6,978,188 B1 | 12/2005 | Christensen |
| 7,029,479 B2 | 4/2006 | Tallarida et al. |
| 7,033,360 B2 | 4/2006 | Cinquin et al. |

(56) References Cited

U.S. PATENT DOCUMENTS

| | | |
|---|---|---|
| 7,039,225 B2 | 5/2006 | Tanaka et al. |
| 7,060,074 B2 | 6/2006 | Rosa et al. |
| 7,074,241 B2 | 7/2006 | McKinnon |
| 7,090,677 B2 | 8/2006 | Fallin et al. |
| 7,094,241 B2 | 8/2006 | Hodorek et al. |
| RE39,301 E | 9/2006 | Bertin |
| 7,104,997 B2 | 9/2006 | Lionberger et al. |
| 7,128,745 B2 | 10/2006 | Masini |
| D532,515 S | 11/2006 | Buttler et al. |
| 7,141,053 B2 | 11/2006 | Rose et al. |
| 7,153,309 B2 | 12/2006 | Huebner et al. |
| 7,174,282 B2 | 2/2007 | Hollister et al. |
| 7,177,386 B2 | 2/2007 | Mostafavi et al. |
| 7,184,814 B2 | 2/2007 | Lang et al. |
| 7,235,080 B2 | 6/2007 | Hodorek |
| 7,238,190 B2 | 7/2007 | Schon et al. |
| 7,239,908 B1 | 7/2007 | Alexander et al. |
| 7,275,218 B2 | 9/2007 | Petrella et al. |
| 7,309,339 B2 | 12/2007 | Cusick et al. |
| 7,340,316 B2 | 3/2008 | Spaeth et al. |
| 7,359,746 B2 | 4/2008 | Arata |
| 7,392,076 B2 | 6/2008 | de La Barrera |
| 7,393,012 B2 | 7/2008 | Funakura et al. |
| 7,394,946 B2 | 7/2008 | Dewaele |
| 7,429,346 B2 | 9/2008 | Ensign et al. |
| 7,468,075 B2 | 12/2008 | Lang et al. |
| 7,517,365 B2 | 4/2009 | Carignan et al. |
| 7,534,263 B2 | 5/2009 | Burdulis, Jr. et al. |
| 7,542,791 B2 | 6/2009 | Mire et al. |
| 7,547,307 B2 | 6/2009 | Carson et al. |
| 7,611,519 B2 | 11/2009 | Lefevre et al. |
| 7,616,800 B2 | 11/2009 | Paik et al. |
| 7,618,421 B2 | 11/2009 | Axelson, Jr. et al. |
| 7,618,451 B2 | 11/2009 | Berez et al. |
| 7,621,744 B2 | 11/2009 | Massoud |
| 7,621,920 B2 | 11/2009 | Claypool et al. |
| 7,630,750 B2 | 12/2009 | Liang et al. |
| 7,634,119 B2 | 12/2009 | Tsougarakis et al. |
| 7,634,306 B2 | 12/2009 | Sarin et al. |
| 7,641,660 B2 | 1/2010 | Lakin et al. |
| 7,641,663 B2 | 1/2010 | Hodorek |
| 7,643,862 B2 | 1/2010 | Schoenefeld |
| 7,658,741 B2 | 2/2010 | Claypool et al. |
| 7,660,623 B2 | 2/2010 | Hunter et al. |
| 7,682,398 B2 | 3/2010 | Croxton et al. |
| 7,693,321 B2 | 4/2010 | Lehtonen-Krause |
| 7,695,520 B2 | 4/2010 | Metzger et al. |
| 7,699,847 B2 | 4/2010 | Sheldon et al. |
| 7,702,380 B1 | 4/2010 | Dean |
| 7,715,602 B2 | 5/2010 | Richard |
| 7,717,956 B2 | 5/2010 | Lang |
| D618,796 S | 6/2010 | Cantu et al. |
| D619,718 S | 7/2010 | Gannoe et al. |
| D622,854 S | 8/2010 | Otto et al. |
| 7,769,429 B2 | 8/2010 | Hu |
| 7,780,672 B2 | 8/2010 | Metzger et al. |
| 7,780,681 B2 | 8/2010 | Sarin et al. |
| 7,796,791 B2 | 9/2010 | Tsougarakis et al. |
| 7,799,077 B2 | 9/2010 | Lang et al. |
| D626,234 S | 10/2010 | Otto et al. |
| 7,806,838 B2 | 10/2010 | Tsai et al. |
| 7,806,896 B1 | 10/2010 | Bonutti |
| 7,815,645 B2 | 10/2010 | Haines |
| 7,824,181 B2 | 11/2010 | Sers |
| 7,842,039 B2 | 11/2010 | Hodorek et al. |
| 7,881,768 B2 | 2/2011 | Lang et al. |
| 7,894,650 B2 | 2/2011 | Weng et al. |
| 7,935,150 B2 | 5/2011 | Carignan et al. |
| 7,940,974 B2 | 5/2011 | Skinner et al. |
| 7,950,924 B2 | 5/2011 | Brajnovic |
| 7,967,868 B2 | 6/2011 | White et al. |
| D642,263 S | 7/2011 | Park |
| 7,974,677 B2 | 7/2011 | Mire et al. |
| 7,981,158 B2 | 7/2011 | Fitz et al. |
| 8,021,368 B2 | 9/2011 | Haines |
| 8,036,729 B2 | 10/2011 | Lang et al. |
| 8,062,302 B2 | 11/2011 | Lang et al. |
| 8,066,708 B2 | 11/2011 | Lang et al. |
| 8,073,521 B2 | 12/2011 | Liew et al. |
| 8,077,950 B2 | 12/2011 | Tsougarakis et al. |
| 8,083,745 B2 | 12/2011 | Lang et al. |
| 8,086,336 B2 | 12/2011 | Christensen |
| 8,092,465 B2 | 1/2012 | Metzger et al. |
| 8,105,330 B2 | 1/2012 | Fitz et al. |
| 8,112,142 B2 | 2/2012 | Alexander et al. |
| 8,122,582 B2 | 2/2012 | Burdulis, Jr. et al. |
| 8,126,533 B2 | 2/2012 | Lavallee |
| RE43,282 E | 3/2012 | Alexander et al. |
| 8,142,189 B2 | 3/2012 | Brajnovic |
| 8,160,345 B2 | 4/2012 | Pavlovskaia et al. |
| 8,167,888 B2 | 5/2012 | Steffensmeier |
| 8,170,716 B2 | 5/2012 | Coste-Maniere et al. |
| 8,175,683 B2 | 5/2012 | Roose |
| 8,206,153 B2 | 6/2012 | Berckmans, III et al. |
| 8,221,430 B2 | 7/2012 | Park et al. |
| 8,234,097 B2 | 7/2012 | Steines et al. |
| 8,265,730 B2 | 9/2012 | Alexander et al. |
| 8,282,646 B2 | 10/2012 | Schoenefeld et al. |
| 8,290,564 B2 | 10/2012 | Lang et al. |
| 8,306,601 B2 | 11/2012 | Lang et al. |
| 8,311,306 B2 | 11/2012 | Pavlovskaia et al. |
| 8,337,501 B2 | 12/2012 | Fitz et al. |
| 8,460,302 B2 | 6/2013 | Park et al. |
| 8,460,303 B2 | 6/2013 | Park |
| 8,480,679 B2 | 7/2013 | Park |
| 8,483,469 B2 | 7/2013 | Pavlovskaia et al. |
| 8,532,361 B2 | 9/2013 | Pavlovskaia et al. |
| D691,719 S | 10/2013 | Park |
| 8,545,509 B2 | 10/2013 | Park et al. |
| 2002/0160337 A1 | 10/2002 | Klein et al. |
| 2003/0009167 A1 | 1/2003 | Wozencroft |
| 2003/0055502 A1 | 3/2003 | Lang et al. |
| 2003/0216669 A1* | 11/2003 | Lang et al. .................. 600/587 |
| 2004/0102792 A1 | 5/2004 | Sarin et al. |
| 2004/0102866 A1* | 5/2004 | Harris et al. .................. 700/117 |
| 2004/0133276 A1 | 7/2004 | Lang et al. |
| 2004/0147927 A1 | 7/2004 | Tsougarakis et al. |
| 2004/0153066 A1 | 8/2004 | Coon et al. |
| 2004/0153087 A1 | 8/2004 | Sanford et al. |
| 2004/0204760 A1* | 10/2004 | Fitz et al. .................. 623/14.12 |
| 2004/0220583 A1 | 11/2004 | Pieczynski, II et al. |
| 2004/0243148 A1 | 12/2004 | Wasielewski |
| 2004/0243481 A1 | 12/2004 | Bradbury et al. |
| 2005/0059978 A1 | 3/2005 | Sherry et al. |
| 2005/0065617 A1 | 3/2005 | de la Barrera et al. |
| 2005/0192588 A1 | 9/2005 | Garcia |
| 2005/0245934 A1 | 11/2005 | Tuke et al. |
| 2005/0245936 A1 | 11/2005 | Tuke et al. |
| 2005/0256389 A1 | 11/2005 | Koga et al. |
| 2005/0267584 A1 | 12/2005 | Burdulis, Jr. et al. |
| 2006/0015018 A1 | 1/2006 | Jutras et al. |
| 2006/0015030 A1 | 1/2006 | Poulin et al. |
| 2006/0015188 A1 | 1/2006 | Grimes |
| 2006/0110017 A1 | 5/2006 | Tsai et al. |
| 2006/0122491 A1 | 6/2006 | Murray et al. |
| 2006/0155293 A1 | 7/2006 | McGinley et al. |
| 2006/0155294 A1 | 7/2006 | Steffensmeier et al. |
| 2006/0195113 A1 | 8/2006 | Masini |
| 2006/0271058 A1 | 11/2006 | Ashton et al. |
| 2007/0021838 A1 | 1/2007 | Dugas et al. |
| 2007/0038059 A1 | 2/2007 | Sheffer et al. |
| 2007/0055268 A1 | 3/2007 | Utz et al. |
| 2007/0073305 A1 | 3/2007 | Lionberger et al. |
| 2007/0083266 A1 | 4/2007 | Lang |
| 2007/0100462 A1 | 5/2007 | Lang et al. |
| 2007/0114370 A1 | 5/2007 | Smith et al. |
| 2007/0118055 A1 | 5/2007 | McCombs |
| 2007/0118243 A1 | 5/2007 | Schroeder et al. |
| 2007/0123912 A1 | 5/2007 | Carson |
| 2007/0162039 A1 | 7/2007 | Wozencroft |
| 2007/0167833 A1 | 7/2007 | Redel et al. |
| 2007/0173858 A1 | 7/2007 | Engh et al. |
| 2007/0191741 A1 | 8/2007 | Tsai et al. |
| 2007/0213738 A1 | 9/2007 | Martin et al. |

(56) References Cited

U.S. PATENT DOCUMENTS

| | | |
|---|---|---|
| 2007/0226986 A1 | 10/2007 | Park et al. |
| 2007/0232959 A1 | 10/2007 | Couture et al. |
| 2007/0233136 A1 | 10/2007 | Wozencroft |
| 2007/0233141 A1 | 10/2007 | Park et al. |
| 2007/0233269 A1 | 10/2007 | Steines et al. |
| 2007/0239167 A1 | 10/2007 | Pinczewski et al. |
| 2007/0249967 A1 | 10/2007 | Buly et al. |
| 2007/0276224 A1 | 11/2007 | Lang et al. |
| 2007/0276400 A1 | 11/2007 | Moore et al. |
| 2008/0004701 A1 | 1/2008 | Axelson et al. |
| 2008/0015599 A1 | 1/2008 | D'Alessio et al. |
| 2008/0015600 A1 | 1/2008 | D'Alessio et al. |
| 2008/0015602 A1 | 1/2008 | Axelson et al. |
| 2008/0015606 A1 | 1/2008 | D'Alessio et al. |
| 2008/0015607 A1 | 1/2008 | D'Alessio et al. |
| 2008/0033442 A1 | 2/2008 | Amiot et al. |
| 2008/0088761 A1 | 4/2008 | Lin et al. |
| 2008/0114370 A1 | 5/2008 | Schoenefeld |
| 2008/0153067 A1 | 6/2008 | Berckmans et al. |
| 2008/0195108 A1 | 8/2008 | Bhatnagar et al. |
| 2008/0234685 A1 | 9/2008 | Gjerde |
| 2008/0257363 A1 | 10/2008 | Schoenefeld et al. |
| 2008/0275452 A1 | 11/2008 | Lang et al. |
| 2008/0287954 A1 | 11/2008 | Kunz et al. |
| 2008/0312659 A1 | 12/2008 | Metzger et al. |
| 2008/0319491 A1 | 12/2008 | Schoenefeld |
| 2009/0024131 A1 | 1/2009 | Metzger et al. |
| 2009/0088763 A1 | 4/2009 | Aram et al. |
| 2009/0093816 A1 | 4/2009 | Roose et al. |
| 2009/0112213 A1 | 4/2009 | Heavener et al. |
| 2009/0131941 A1 | 5/2009 | Park et al. |
| 2009/0138020 A1 | 5/2009 | Park et al. |
| 2009/0151736 A1 | 6/2009 | Belcher et al. |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0222103 A1 | 9/2009 | Fitz et al. |
| 2009/0248044 A1 | 10/2009 | Amiot et al. |
| 2009/0254093 A1 | 10/2009 | White et al. |
| 2009/0254367 A1 | 10/2009 | Belcher et al. |
| 2009/0276045 A1 | 11/2009 | Lang |
| 2009/0306676 A1 | 12/2009 | Lang et al. |
| 2009/0312805 A1 | 12/2009 | Lang et al. |
| 2010/0023015 A1 | 1/2010 | Park |
| 2010/0042105 A1 | 2/2010 | Park et al. |
| 2010/0152741 A1 | 6/2010 | Park et al. |
| 2010/0160917 A1 | 6/2010 | Fitz et al. |
| 2010/0168754 A1 | 7/2010 | Fitz et al. |
| 2010/0174376 A1 | 7/2010 | Lang |
| 2010/0228257 A1 | 9/2010 | Bonutti |
| 2010/0256479 A1 | 10/2010 | Park et al. |
| 2010/0274534 A1 | 10/2010 | Steines et al. |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0329530 A1 | 12/2010 | Lang et al. |
| 2011/0029093 A1 | 2/2011 | Bojarski et al. |
| 2011/0066193 A1 | 3/2011 | Lang et al. |
| 2011/0066245 A1 | 3/2011 | Lang et al. |
| 2011/0071581 A1 | 3/2011 | Lang et al. |
| 2011/0087332 A1 | 4/2011 | Bojarski et al. |
| 2011/0214279 A1 | 9/2011 | Park |
| 2011/0268248 A1 | 11/2011 | Simon et al. |
| 2011/0276145 A1 | 11/2011 | Carignan et al. |
| 2011/0295329 A1 | 12/2011 | Fitz et al. |
| 2011/0295378 A1 | 12/2011 | Bojarski et al. |
| 2012/0053591 A1 | 3/2012 | Haines et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0093377 A1 | 4/2012 | Tsougarakis et al. |
| 2012/0101503 A1 | 4/2012 | Lang et al. |
| 2012/0143197 A1 | 6/2012 | Lang et al. |
| 2012/0151730 A1 | 6/2012 | Fitz et al. |
| 2012/0158001 A1 | 6/2012 | Burdulis, Jr. et al. |
| 2012/0158002 A1 | 6/2012 | Carignan et al. |
| 2012/0165821 A1 | 6/2012 | Carignan et al. |
| 2012/0191205 A1 | 7/2012 | Bojarski et al. |
| 2012/0191420 A1 | 7/2012 | Bojarski et al. |
| 2012/0197260 A1 | 8/2012 | Fitz et al. |
| 2012/0197408 A1 | 8/2012 | Lang et al. |
| 2012/0215226 A1 | 8/2012 | Bonutti |
| 2012/0230566 A1 | 9/2012 | Dean et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski et al. |
| 2012/0310400 A1 | 12/2012 | Park |
| 2013/0115474 A1 | 5/2013 | Park |
| 2013/0116697 A1 | 5/2013 | Park et al. |
| 2013/0123789 A1 | 5/2013 | Park |
| 2013/0190767 A1 | 7/2013 | Park et al. |
| 2013/0197526 A1 | 8/2013 | Park et al. |
| 2013/0197687 A1 | 8/2013 | Pavlovskaia et al. |

FOREIGN PATENT DOCUMENTS

| | | |
|---|---|---|
| DE | 102005023028 A1 | 11/2006 |
| EP | 0097001 A | 12/1983 |
| EP | 0574098 A | 12/1993 |
| EP | 0622052 A | 11/1994 |
| EP | 0908836 A2 | 4/1999 |
| EP | 0908836 A3 | 12/1999 |
| EP | 1059153 A2 | 12/2000 |
| EP | 1486900 A1 | 12/2004 |
| EP | 1532939 A1 | 5/2005 |
| GB | 2215610 A1 | 9/1989 |
| GB | 2420717 A | 6/2006 |
| JP | 10-94538 | 4/1998 |
| JP | 2001-092950 | 4/2001 |
| WO | WO 93/25157 A1 | 12/1993 |
| WO | WO 95/07509 A1 | 3/1995 |
| WO | WO 95/27450 | 10/1995 |
| WO | WO 97/23172 A2 | 7/1997 |
| WO | WO 98/12995 A2 | 4/1998 |
| WO | WO 00/35346 | 6/2000 |
| WO | WO 01/00096 A1 | 1/2001 |
| WO | WO 01/70142 A1 | 9/2001 |
| WO | WO 01/85040 A1 | 11/2001 |
| WO | WO 02/096268 A2 | 12/2002 |
| WO | WO 2004/032806 A1 | 4/2004 |
| WO | WO 2004/049981 A2 | 6/2004 |
| WO | WO 2005/051240 A1 | 6/2005 |
| WO | WO 2005/087125 A2 | 9/2005 |
| WO | WO 2006/058057 A2 | 6/2006 |
| WO | WO 2006/060795 A1 | 6/2006 |
| WO | WO 2006/092600 A1 | 9/2006 |
| WO | WO 2006/134345 A1 | 12/2006 |
| WO | WO 2007/014164 A2 | 2/2007 |
| WO | WO 2007/058632 A1 | 5/2007 |
| WO | WO 2007/092841 A2 | 8/2007 |

OTHER PUBLICATIONS

Advisory Action, U.S. Appl. No. 11/642,385, dated Oct. 29, 2010, 3 pages.
Amendment and Response to Ex Parte Quayle Action, U.S. Appl. No. 29/296,687 dated Mar. 24, 2011, 17 pages.
Amendment and Response to Final Office Action, U.S. Appl. No. 11/642,385, filed Oct. 4, 2010, 16 pages.
Amendment and Response to Non-Final Office Action, U.S. Appl. No. 11/641,382, dated Apr. 20, 2010, 23 pages.
Amendment and Response to Non-Final Office Action, U.S. Appl. No. 11/959,344, dated Jul. 15, 2011, 13 pages.
Amendment and Response to Office Action and Petition to Revive, U.S. Appl. No. 10/146,862, filed Jan. 18, 2006, 29 pages.
Amendment and Response to Office Action, U.S. Appl. No. 11/656,323, filed Jun. 25, 2010, 7 pages.

(56) References Cited

OTHER PUBLICATIONS

Amendment and Response to Office Action, U.S. Appl. No. 11/641,569, dated Feb. 5, 2010, 20 pages.
Amendment and Response to Restriction Requirement, U.S. Appl. No. 11/641,569, dated May 27, 2009, 12 pages.
Amendment and Response to Restriction Requirement, U.S. Appl. No. 11/641,382, dated Oct. 5, 2009, 10 pages.
Amendment and Response to Restriction Requirement, U.S. Appl. No. 11/642,385, filed Nov. 24, 2009, 10 pages.
Amendment and Response to Restriction/Election Requirement, U.S. Appl. No. 11/656,323, filed Dec. 8, 2009, 6 pages.
Amendment and Response, U.S. Appl. No. 11/642,385, filed May 28, 2010, 11 pages.
Amendment Under 37 C.F.R. 1.312, U.S. Appl. No. 12/386,105, filed Oct. 1, 2012, 6 pages.
Appeal Brief, U.S. Appl. No. 12/390,667, filed Jul. 12, 2012, 32 pages.
Appeal Brief, U.S. Appl. No. 12/391,008, filed Oct. 16, 2012, 24 pages.
European Search Report, 10192631.9-2310, dated Mar. 17, 2011, 5 pages.
Ex Parte Quayle Action, U.S. Appl. No. 29/296,687, mailed Jan. 24, 2011, 11 pages.
Examiner's Answer in appeal, U.S. Appl. No. 12/391,008, mailed Dec. 13, 2012, 27 pages.
Final Office Action, U.S. Appl. No. 11/641,382, mailed Aug. 5, 2010, 13 pages.
Final Office Action, U.S. Appl. No. 11/656,323, mailed Sep. 3, 2010, 11 pages.
Final Office Action, U.S. Appl. No. 11/641,569, mailed May 10, 2010, 9 pages.
Final Office Action, U.S. Appl. No. 11/959,344, mailed Oct. 27, 2011, 12 pages.
Final Office Action, U.S. Appl. No. 12/390,667, mailed Jan. 13, 2012, 27 pages.
Final Office Action, U.S. Appl. No. 12/546,545, dated Dec. 20, 2012, 16 pages.
Final Office Action, U.S. Appl. No. 12/636,939, mailed Jan. 25, 2013, 9 pages.
Final Office Action, U.S. Appl. No. 11/641,382, mailed Jul. 25, 2012, 12 pages.
Final Office Action, U.S. Appl. No. 11/641,569, mailed Mar. 1, 2012, 12 pages.
Final Office Action, U.S. Appl. No. 11/924,425, mailed Jul. 6, 2012, 14 pages.
Final Office Action, U.S. Appl. No. 11/946,002, mailed May 9, 2012, 24 pages.
Final Office Action, U.S. Appl. No. 12/391,008, mailed May 17, 2012, 28 pages.
Final Office Action, U.S. Appl. No. 12/563,809, mailed Mar. 7, 2013, 14 pages.
International Search Report and Written Opinion, International Application No. PCT/US2009/034983, mailed May 22, 2009, 15 pages.
International Search Report and Written Opinion, International Application No. PCT/US2009/034967, mailed Jun. 16, 2009, 15 pages.
International Search Report and Written Opinion, International Application No. PCT/US2009/041519, mailed Jun. 17, 2009, 10 pages.
International Search Report and Written Opinion, International Application No. PCT/US2009/040629, mailed Aug. 6, 2009, 9 pages.
International Search Report and Written Opinion, International Application No. PCT/US2009/051109, mailed Nov. 6, 2009, 13 pages.
International Search Report and Written Opinion, International Application No. PCT/US2009/058946, mailed Jan. 28, 2010, 14 pages.
International Search Report and Written Opinion, International Application No. PCT/US2009/068055, mailed Mar. 11, 2010, 10 pages.
International Search Report and Written Opinion, PCT/US2007/001624, dated Dec. 12, 2007, 14 pages.
International Search Report and Written Opinion, PCT/US2007/001622, dated Jun. 11, 2007, 14 pages.
International Search Report and Written Opinion, PCT/US2008/083125, dated Mar. 9, 2009, 13 pages.
International Search Report and Written Opinion, PCT/US2011/032342, dated Jul. 1, 2011, 8 pages.
Invitation to Pay Additional Fees mailed on Jul. 31, 2007, for PCT Application No. PCT/US2007/001624 filed on Jan. 19, 2007, 5 pages.
Non-Final Office Action, U.S. Appl. No. 11/641,382, mailed Jan. 20, 2010, 12 pages.
NonFinal Office Action, U.S. Appl. No. 11/642,385, mailed Mar. 2, 2010, 11 pages.
Non-Final Office Action, U.S. Appl. No. 11/656,323, mailed Mar. 30, 2010, 10 pages.
Non-Final Office Action, U.S. Appl. No. 11/641,569, dated Aug. 3, 2011, 14 pages.
Non-Final Office Action, U.S. Appl. No. 11/641,569, dated Jan. 3, 2013, 12 pages.
Non-Final Office Action, U.S. Appl. No. 11/924,425, mailed Jan. 25, 2012, 35 pages.
Non-Final Office Action, U.S. Appl. No. 12/390,667, dated Aug. 24, 2011, 49 pages.
Non-Final Office Action, U.S. Appl. No. 13/086,275, mailed Feb. 7, 2013, 36 pages.
Non-Final Office Action, U.S. Appl. No. 11/641,382, mailed Mar. 29, 2012, 24 pages.
Non-Final Office Action, U.S. Appl. No. 11/641,569, mailed Jul. 12, 2013, 21 pages.
NonFinal Office Action, U.S. Appl. No. 11/641,569, mailed Nov. 12, 2009, 9 pages.
Non-Final Office Action, U.S. Appl. No. 11/946,002, dated Nov. 25, 2011, 44 pages.
Nonfinal Office Action, U.S. Appl. No. 11/959,344, dated Feb. 15, 2011, 29 pages.
Non-Final Office Action, U.S. Appl. No. 12/111,924, mailed Jun. 29, 2012, 35 pages.
Non-Final Office Action, U.S. Appl. No. 12/386,105, dated Feb. 9, 2012, 30 pages.
Non-Final Office Action, U.S. Appl. No. 12/390,667, mailed Sep. 26, 2012, 21 pages.
Non-Final Office Action, U.S. Appl. No. 12/391,008, mailed Oct. 31, 2011, 44 pages.
Non-Final Office Action, U.S. Appl. No. 12/546,545, mailed Jul. 19, 2012, 28 pages.
Non-Final Office Action, U.S. Appl. No. 12/546,545, mailed Mar. 13, 2013, 10 pages.
Non-Final Office Action, U.S. Appl. No. 12/563,809, mailed Sep. 21, 2012, 32 pages.
Non-Final Office Action, U.S. Appl. No. 12/636,939, mailed Jul. 20, 2012, 25 pages.
Non-Final Office Action, U.S. Appl. No. 13/374,960, mailed Aug. 1, 2012, 6 pages.
Notice of Allowance, U.S. Appl. No. 11/641,382, mailed Feb. 6, 2013, 14 pages.
Notice of Allowance, U.S. Appl. No. 11/924,425, mailed Feb. 5, 2013, 16 pages.
Notice of Allowance, U.S. Appl. No. 12/111,924, dated Dec. 24, 2012, 10 pages.
Notice of Allowance, U.S. Appl. No. 13/066,568, mailed Oct. 26, 2011, 28 pages.
Notice of Allowance, U.S. Appl. No. 29/394,882, mailed Feb. 4, 2013, 32 pages.
Notice of Allowance, U.S. Appl. No. 11/641,382, mailed Oct. 9, 2012, 9 pages.
Notice of Allowance, U.S. Appl. No. 11/924,425, mailed Sep. 25, 2012, 18 pages.

(56) References Cited

OTHER PUBLICATIONS

Notice of Allowance, U.S. Appl. No. 11/959,344, mailed Mar. 5, 2012, 13 pages.
Notice of Allowance, U.S. Appl. No. 12/111,924, mailed Mar. 11, 2013, 14 pages.
Notice of Allowance, U.S. Appl. No. 12/386,105, mailed Jul. 5, 2012, 11 pages.
Notice of Allowance, U.S. Appl. No. 13/374,960, mailed Nov. 2, 2012, 24 pages.
Notice of Allowance, U.S. Appl. No. 13/573,662, mailed Mar. 19, 2013, 34 pages.
Notice of Allowance, U.S. Appl. No. 29/296,687, mailed Mar. 31, 2011, 18 pages.
Notice of Non-Compliant Amendment, U.S. Appl. No. 11/641,569, mailed Aug. 7, 2009, 3 pages.
Office Action (Restriction Requirement), U.S. Appl. No. 12/563,809, dated Feb. 2, 2012, 7 pages.
Office Action, U.S. Appl. No. 10/146,862, mailed Jan. 13, 2005, 10 pages.
Preliminary Amendment, U.S. Appl. No. 11/641,569, dated Aug. 14, 2008, 13 pages.
Preliminary Amendment, U.S. Appl. No. 11/642,385, filed Aug. 22, 2008, 42 pages.
RCE/Amendment, U.S. Appl. No. 11/641,569, filed Aug. 9, 2010, 18 pages.
RCE/Amendment, U.S. Appl. No. 11/642,382, filed Oct. 26, 2010, 14 pages.
RCE/Amendment, U.S. Appl. No. 11/642,385, filed Dec. 6, 2010, 13 pages.
RCE/Amendment, U.S. Appl. No. 11/656,323, filed Nov. 19, 2010, 12 pages.
RCE/Amendment, U.S. Appl. No. 11/946,002, filed Sep. 6, 2012, 38 pages.
Response to Final Office Action, U.S. Appl. No. 12/546,545, filed Feb. 20, 2013, 13 pages.
Response to Final Office Action, U.S. Appl. No. 11/641,569, filed Jun. 28, 2012, 10 pages.
Response to Final Office Action, U.S. Appl. No. 11/641,382, filed Sep. 24, 2012, 11 pages.
Response to Final Office Action, U.S. Appl. No. 11/959,344, filed Dec. 27, 2011, 16 pages.
Response to Final Office Action, U.S. Appl. No. 11/924,425, filed Sep. 5, 2012, 9 pages.
Response to Final Office Action, U.S. Appl. No. 12/390,667, filed Mar. 12, 2012, 19 pages.
Response to Non-Final Office Action, U.S. Appl. No. 12/390,667, filed Feb. 26, 2013, 36 pages.
Response to Non-Final Office Action, U.S. Appl. No. 12/563,809, filed Dec. 13, 2012, 15 pages.
Response to Non-Final Office Action, U.S. Appl. No. 12/390,667, filed Nov. 18, 2011, 16 pages.
Response to Non-Final Office Action, U.S. Appl. No. 11/641,569, filed Dec. 2, 2011, 7 pages.
Response to Non-Final Office Action, U.S. Appl. No. 12/391,008, filed Feb. 24, 2012, 18 pages.
Response to Non-Final Office Action, U.S. Appl. No. 11/946,002, filed Mar. 8, 2012, 16 pages.
Response to Non-Final Office Action, U.S. Appl. No. 11/924,425, filed Apr. 25, 2012, 8 pages.
Response to Non-Final Office Action, U.S. Appl. No. 12/386,105, filed Jun. 8, 2012, 13 pages.
Response to Non-Final Office Action, U.S. Appl. No. 11/641,382, filed Jun. 27, 2012, 12 pages.
Response to Non-Final Office Action, U.S. Appl. No. 12/111,924, filed Sep. 28, 2012, 10 pages.
Response to Non-Final Office Action, U.S. Appl. No. 12/636,939, filed Oct. 10, 2012, 8 pages.
Response to Non-Final Office Action, U.S. Appl. No. 12/546,545, filed Oct. 19, 2012, 15 pages.
Response to Non-Final Office Action, U.S. Appl. No. 11/641,569, filed Apr. 3, 2013, 9 pages.
Response to Notice of Non-Complaint Amendment, U.S. Appl. No. 11/641,569, dated Aug. 19, 2009, 11 pages.
Response to Restriction Requirement U.S. Patent Application No. 29/296,687, filed Oct. 7, 2010, 3 pages.
Response to Restriction Requirement, U.S. Appl. No. 11/959,344, filed Nov. 24, 2010, 13 pages.
Response to Restriction Requirement, U.S. Appl. No. 12/390,667, dated Jul. 27, 2011, 8 pages.
Response to Restriction Requirement, U.S. Appl. No. 12/391,008, filed Aug. 29, 2011, 9 pages.
Response to Restriction Requirement, U.S. Appl. No. 12/386,105, filed Dec. 21, 2011, 9 pages.
Response to Restriction Requirement, U.S. Appl. No. 12/563,809, filed Feb. 24, 2012, 10 pages.
Response to Restriction Requirement, U.S. Appl. No. 12/111,924, filed Apr. 16, 2012, 8 pages.
Response to Restriction Requirement, U.S. Appl. No. 12/636,939, filed Apr. 19, 2012, 6 pages.
Response to Restriction, U.S. Appl. No. 12/563,809, filed Aug. 6, 2012, 10 pages.
Response to Restriction, U.S. Appl. No. 11/924,425, filed Nov. 8, 2011, 5 pages.
Response to Restriction, U.S. Appl. No. 11/946,002, filed Sep. 23, 2011, 7 pages.
Response to Restriction, U.S. Appl. No. 12/505,056, filed Apr. 11, 2012, 9 pages.
Response to Restriction, U.S. Appl. No. 12/546,545, filed Jun. 4, 2012, 7 pages.
Response to Restriction, U.S. Appl. No. 13/573,662, filed Feb. 8, 2013, 8 pages.
Restriction Requirement, U.S. Appl. No. 13/573,662, mailed Jan. 17, 2013, 6 pages.
Restriction Requirement, U.S. Appl. No. 11/641,382, mailed Sep. 3, 2009, 6 pages.
Restriction Requirement, U.S. Appl. No. 11/641,569, mailed Apr. 27, 2009, 7 pages.
Restriction Requirement, U.S. Appl. No. 11/642,385, mailed Oct. 27, 2009, 7 pages.
Restriction Requirement, U.S. Appl. No. 11/656,323, mailed Nov. 13, 2009, 10 pages.
Restriction Requirement, U.S. Appl. No. 11/924,425, dated Oct. 13, 2011, 6 pages.
Restriction Requirement, U.S. Appl. No. 11/946,002, dated Sep. 1, 2011, 8 pages.
Restriction Requirement, U.S. Appl. No. 11/959,344, dated Oct. 29, 2010, 6 pages.
Restriction Requirement, U.S. Appl. No. 12/111,924, mailed Mar. 19, 2012, 8 pages.
Restriction Requirement, U.S. Patent Application No. 12/386,105, dated Oct. 24, 2011, 7 pages.
Restriction Requirement, U.S. Appl. No. 12/390,667, dated Jul. 14, 2011, 9 pages.
Restriction Requirement, U.S. Appl. No. 12/391,008, dated Aug. 18, 2011, 6 pages.
Restriction Requirement, U.S. Appl. No. 12/505,056, mailed Mar. 14, 2012, 8 pages.
Restriction Requirement, U.S. Appl. No. 12/546,545, mailed May 3, 2012, 8 pages.
Restriction Requirement, U.S. Appl. No. 12/563,809, mailed Jul. 6, 2012, 6 pages.
Restriction Requirement, U.S. Appl. No. 12/636,939, mailed Apr. 13, 2012, 6 pages.
Restriction Requirement, U.S. Appl. No. 12/760,388, mailed Mar. 6, 2013, 7 pages.
Restriction Requirement, U.S. Appl. No. 29/296,687, mailed Sep. 21, 2010, 7 pages.
Akca, "Matching of 3D Surfaces and Their Intensities," ISPRS Journal of Photogrammetry & Remote Sensing, 62(2007), 112-121.
Akenine-Möller et al., *Real-Time Rendering, Second Edition*, AK Peters, Natick, MA, 6 pages (Table of Contents), 2002.

(56) References Cited

OTHER PUBLICATIONS

Arima et al., "Femoral Rotational Alignment, Based on the Anteroposterior Axis, in Total Knee Arthroplasty in a Valgus Knee. A Technical Note," Journal Bone Joint Surg Am. 1995;77(9):1331-4.

Author Unknown, "MRI Protocol Reference," ConforMIS, Inc., copyright 2007, http://www.conformis.com/Imaging-Professionals/MRI-Protocol-Guides, last visited on Mar. 28, 2008, 18 pages.

Author Unknown, "MRI Protocol Reference Guide for GE Systems," ConforMIS, Inc., copyright 2007, http://www.conformis.com/Imaging-Professionals/MRI-Protocol-Guides, last visited on Mar. 28, 2008, 18 pages.

Author Unknown, "MRI Protocol Reference Guide for Phillips Systems," ConforMIS, Inc., copyright 2007, http://www.conformis.com/Imaging-Professionals/MRI-Protocol-Guides, last visited on Mar. 28, 2008, 19 pages.

Author Unknown, "MRI Protocol Reference Guide for Siemens Systems," ConforMIS, Inc., copyright 2007, http://www.conformis.com/Imaging-Professionals/MRI-Protocol-Guides, last visited on Mar. 28, 2008, 18 pages.

Barequet et al., "Filling Gaps in the Boundary of a Polyhedron," Computer Aided Geometric Design, vol. 12, pp. 207-229, 1995.

Barequet et al., "Repairing CAD Models," Proceedings of the 8th IEEE Visualization '97 Conference, pp. 363-370, Oct. 1997.

Bargar et al., "Robotic Systems in Surgery," Orthopedic and Spine Surgery, Surgical Technology International II, 1993, 419-423.

Berry et al., "Personalised image-based templates for intra-operative guidance," Proc. Inst. Mech. Eng. Part H: J. Engineering in Medicine, vol. 219, pp. 111-118, Oct. 7, 2004.

Besl et al., "A Method for Registration of 3-D Shapes," IEEE Transactions on Pattern Analysis and Machine Intelligence (PAMI), 14(2):239-256, Feb. 1992.

Biščević et al., "Variations of Femoral Condyle Shape," Coll. Antropol., vol. 29 No. 2, pp. 409-414, 2005.

Blaha et al., "Using the Transepicondylar Axis to Define the Sagittal Morphology of the Distal Part of the Femur," J Bone Joint Surg Am. 2002;84-A Suppl 2:48-55.

Blinn, Jim Blinn's Corner—A Trip Down the Graphics Pipeline, Morgan Kaufmann Publishers, Inc., San Francisco, CA, 5 pages (Table of Contents), 1996.

Bøhn et al., "A Topology-Based Approach for Shell-Closure," Geometric Modeling for Product Realization (P.R. Wilson et al. editors), pp. 297-319, Elsevier Science Publishers B.V., North-Holland, 1993.

Bullough et al., "The Geometry of Diarthrodial Joints, Its Physiologic Maintenance and the Possible significance of Age-Related Changes in Geometry-to-Load distribution and the Development of Osteoarthritis," Clin Orthop Rel Res 1981, 156:61-6.

Burgkart et al., "Magnetic Resonance Imaging-Based Assessment of Cartilage Loss in Severe Osteoarthritis: Accuracy, Precision, and Diagnostic Value," Arthritis Rheum 2001, 44:2072-7.

Canny, "A computational Approach to Edge Detection," IEEE Transactions on Pattern Analysis and Machine Intelligence, PAMI 8(6), pp. 679-698 (1986).

Chauhan et al., "Computer-assisted knee arthroplasty versus a conventional jig-based technique—a randomised, prospective trial," The Journal of Bone and Joint Surgery, vol. 86-B, No. 3, pp. 372-377, Apr. 2004.

Churchill et al., "The Transepicondylar Axis Approximates the Optimal Flexion Axis of the Knee," Clin Orthop Relat Res. 1998(356):111-8.

Cicuttini et al., "Gender Differences in Knee Cartilage Volume as Measured by Magnetic Resonance Imaging," Osteoarthritis Cartilage 1999, 7:265-71.

Cicuttini et al., "Longitudinal Study of the Relationship Between Knee angle and Tibiofemoral cartilage Volume in Subjects with Knee Osteoarthritis," Rheumatology (Oxford) 2004, 43:321-4.

Cohen et al., Radiosity and Realistic Image Synthesis, Academic Press Professional, Cambridge, MA, 8 pages. (Table of Contents), 1993.

Couglin et al., "Tibial Axis and Patellar Position Relative to the Femoral Epicondylar Axis During Squatting," The Journal of Arthroplasty, vol. 18, No. 8, Elsevier, 2003.

Delp et al., "Computer Assisted Knee Replacement," Clinical Orthopaedics and Related Research, No. 354, pp. 49-56, Sep. 1998.

Dutré et al., Advanced Global Illumination, AK Peters, Natick, MA, 5 pages (Table of Contents), 2003.

Eckhoff et al., "Difference Between the Epicondylar and Cylindrical Axis of the Knee," Clin Orthop Relat Res. 2007;461:238-44.

Eckhoff et al., "Three-Dimensional Mechanics, Kinematics, and Morphology of the Knee Viewed in Virtual Realty," The Journal of Bone and Joint Surgery, vol. 87-A, Supplement 2, pp. 71-80, 2005.

Eisenhart-Rothe et al., "Femorotibial and Patellar Cartilage Loss in Patients Prior to Total Knee arthroplasty, Heterogeneity, and Correlation with alignment of the Knee," Ann Rheum Dis., Jun. 2005 (BMJ Publishing Group Ltd & European League Against Rheumatism).

Eisenhart-Rothe et al., "The Role of Knee alignment in Disease Progression and Functional Decline in Knee Osteoarthritis," JAMA 2001, 286:188-95.

Elias et al., "A Correlative Study of the Geometry and anatomy of the Distal Femur," Clin orthop Relat Res. 1990(260):98-103.

Erikson, "Error Correction of a Large Architectural Model: The Henderson County Courthouse," Technical Report TR95-013, Dept. of Computer Science, University of North Carolina at Chapel Hill, pp. 1-11, 1995.

Ervin et al., Landscape Modeling, McGraw-Hill, New York, NY, 8 pages (Table of Contents), 2001.

Farin, NURB Curves and Surfaces: From Projective Geometry to Practical Use, AK Peters, Wellesley, MA, 7 pages (Table of Contents), 1995.

Favorito et al., "Total Knee Arthroplasty in the Valgus Knee," Journal Am Acad Orthop surg. 2002;10(1):16-24.

Fleischer et al., "Accurate Polygon Scan Conversion Using Half-Open Intervals," Graphics Gems III, pp. 362-365, code: pp. 599-605, 1992.

Foley et al., Computer Graphics: Principles and Practice, Addison-Wesley Publishing Company, Reading, MA, 9 pages (Table of Contents), 1990.

Freeman et al., "The Movement of the Knee Studied by Magnetic Resonance Imaging," Clinical orthop Relat Res. 2003(410):35-43.

Freeman et al., "The Movement of the Normal Tibio-Femoral Joint," Journal Biomech. 2005;38(2):197-208.

Glassner (editor), An Introduction to Ray Tracing, Academic Press Limited, San Diego, CA, 4 pages (Table of Contents), 1989.

Glassner, Principles of Digital Image Synthesis, vols. One and Two, Morgan Kaufmann Publishers, Inc., San Francisco, CA, 32 pages (Table of Contents), 1995.

Gooch et al., Non-Photorealistic Rendering, AK Peters, Natick, MA, 4 pages (Table of Contents), 2001.

Graichen et al., "Quantitative Assessment of Cartilage Status in Osteoarthritis by Quantitative Magnetic Resonance Imaging: Technical Validation for Use in analysis of Cartilage Volume and Further Morphologic Parameters," Arthritis Rheum 2004, 50:811-16.

Gruen et al., "Least Squares 3D Surface and Curve Matching," ISPRS Journal of Photogrammetry & Remote Sensing, 59(2005), 151-174.

Grüne et al., "On numerical algorithm and interactive visualization for optimal control problems," Journal of Computation and Visualization in Science, vol. 1, No. 4, pp. 221-229, Jul. 1999.

Guéziec et al., "Converting Sets of Polygons to Manifold Surfaces by Cutting and Stitching," Proc. IEEE Visualization 1998, pp. 383-390, Oct. 1998.

Hafez et al., "Patient Specific Instrumentation for TKA: Testing the Reliability Using a Navigational System," MIS Meets CAOS Symposium & Instructional Academy, Less and Minimally Invasive Surgery for Joint Arthroplasty: FACT and FICTION Syllabus, San Diego, CA, 8 pages, Oct. 20-22, 2005.

Hafez et al., "Computer Assisted Total Knee Replacement: Could a Two-Piece Custom Template Replace the Complex Conventional Instrumentations?", Computer Aided Surgery, vol. 9, No. 3, pp. 93-94, 2004.

Hafez et al., "Computer-Assisted Total Knee Arthroplasty Using Patient-Specific Templating," Clinical Orthopaedics and Related Research, No. 0, pp. 1-9, 2006.

(56) References Cited

OTHER PUBLICATIONS

Hollister et al., "The Axes of Rotation of the Knee," Clin Orthop Relat Res. 1993(290):259-68.

Howell et al., "Longitudinal Shapes of the Tibia and Femur are Unrelated and Variable," Clinical Orthopaedics and Related Research (2010) 468: 1142-1148.

Howell et al., "Results of an Initial Experience with Custom-Fit Positioning Total Knee Arthroplasty in a Series of 48 Patients," Orthopedics, 2008;31(9):857-63.

Howell et al., "In Vivo Adduction and Reverse Axial Rotation (External) of the Tibial Component can be Minimized During Standing and Kneeling," OrthopedicslORTHOSupersite.com vol. 32 No. 5, 319-326 (May 2009).

Iwaki et al., "Tibiofemoral Movement 1: The Shapes and Relative Movements of the Femur and Tibia in the Unloaded Cadaver Knee," Journal Bone Joint Surg Br. 2000;82(8):1189-95.

Jensen, *Realistic Image Synthesis Using Photon Mapping*, AK Peters, Natick, MA, 7 pages (Table of Contents), 2001.

Jacobs et al., "Hip Resurfacing Through an Anterolateral Approach," J. Bone Joint Surg Am. 2008:90 Suppl 3:38-44.

Johnson, "Joint Remodeling as the Basis for Osteoarthritis," Journal Am Vet Med Assoc. 1962, 141:1233-41.

Jones et al., "A new approach to the construction of surfaces from contour data," *Computer Graphics Forum*, vol. 13, No. 3, pp. 75-84, 1994 [ISSN 0167-7055].

Kass et al., "Active Contour Models," International Journal of Computer Vision, pp. 321-331 (1988).

Kellgren et al., "Radiological Assessment of Osteoarthrosis," Ann Rheum Dis 1957, 10:494-501.

Kessler et al, "Sagittal Curvature of Total Knee Replacements Predicts in vivo Kinematics," Clin Biomech (Bristol, Avon) 2007; 22(1):52-8.

Khorramabadi, "A Walk Through the Planned CS Building," Technical Report UCB/CSD 91/652, Computer Science Department, University of California at Berkeley, 74 pages, 1991.

Kidder et al., "3-D Model Acquisition, Design, Planning and Manufacturing of Orthopaedic Devices: A Framework," *Advanced Sensor and Control-System Interface* (B.O. Nnaji editor), Proceedings SPIE—The International Society for Optical Engineering, Bellingham, WA, vol. 2911, pp. 9-22, Nov. 21-22, 1996.

Kienzel III et al., "Total Knee Replacement," IEEE May/Jun. 1995.

Kienzel III et al., "An Integrated CAD-Robotics System for Total Knee Replacement Surgery", IEEE International Conference, pp. 889-894, vol. 1, May 1993.

Krackow et al., "Flexion-Extension Joint Gap Changes After Lateral Structure Release for Valgus Deformity Correction in Total Knee Arthroplasty: A Cadaveric Study," Journal Arthroplasty, 1999;14(8):994-1004.

Krackow et al., "Primary Total Knee Arthroplasty in Patients with Fixed Valgus Deformity," Clin Orthop Relat Res. 1991(273):9-18.

Krackow, "Approaches to Planning lower Extremity alignment for Total Knee arthroplasty and Osteotomy About the Knee," adv Orthop surg 7:69, 1983.

Kumar, *Robust Incremental Polygon Triangulation for Surface Rendering*, Center for Geometric Computing, Department of Computer Science, Johns Hopkins University, Baltimore, MD, WSCG, The International Conference in Central Europe on Computer Graphics, Visualization and Computer Vision, pp. 381-388, 2000.

Kunz et al., "Computer Assisted Hip Resurfacing Using Individualized Drill Templates," *The Journal of Arthroplasty*, vol. 00, No. 0, pp. 1-7, 2009.

Kusumoto et al., "Application of Virtual Reality Force Feedback Haptic Device for Oral Implant Surgery", Graduate School of Dentistry Course for Integrated Oral Science and Stomatology, Jun. 16, 2005.

Lea et al., "Registration and immobilization in robot-assisted surgery", Journal of Image Guided Surgery, pp. 1-10, 1995.

Lorensen et al., "Marching Cubes: A High Resolution 3d Surface Construction Algorithm," *Computer Graphics*, vol. 21, No. 4, pp. 163-169, 1987.

Manner et al., "Knee Deformity in Congenital Longitudinal Deficiencies of the Lower Extremity," Clin Orthop Relat Res. 2006;448:185-92.

Matsuda et al., "Anatomical Analysis of the Femoral Condyle in Normal and Osteoarthritic Knees," Journal Orthopaedic Res. 2004;22(1):104-9.

Matsuda et al., "Femoral Condyle Geometry in the Normal and Varus Knee," Clinical Orthop Relat Res. 1998(349):183-8.

Messmer et al., "Volumetric Determination of the Tibia Based on 2d Radiographs Using a 2d/3d Database", Dept. of Surgery, Trauma Unit, University Hospital, Bassel, Switzerland, *Computer Aided Surgery* 6:183-194 (2001).

Mihalko et al., The Variability of Intramedullary Alignment of the Femoral Component During Total Knee Arthroplasty, Journal Arthroplasty. 2005;20(1):25-8.

Mole et al., "A New Three-Dimensional Treatment Algorithm for Complex Surfaces: Applications in Surgery", Feb. of 1995.

Morvan et al., IVECS, Interactively Correcting .STL Files in a Virtual Environment, Clemson University, Clemson, SC, Proc. Conf. Virtual Design, Aug. 1996.

Nooruddin et al., Simplification and Repair of Polygonal Models Using Volumetric Techniques, *IEEE Transactions on Visualization and Computer Graphics*, vol. 9, No. 2, pp. 191-205, Apr.-Jun. 2003.

Panjabi et al., "Errors in Kinematic Parameters of a Planar Joint: Guidelines for Optimal Experimental Design," Journal Biomech. 1982;15(7):537-44.

Perillo-Marcone et al., "Effect of Varus/Valgus Malalignment on Bone Strains in the Proximal Tibia After TKR: An Explicit Finite element Study," Journal Biomechanical Engineering 2007, vol. 129, 1:1-11.

Peterfy et al., "Quantification of articular Cartilage in the Knee with Pulsed Saturation Transfer Subtraction and Fact-Suppressed MR Imaging: Optimization and Validation," Radiology 1994, 192:485-91.

Pinskerova et al., "The Shapes and Relative Movements of the Femur and Tibia at the Knee," Orthopaedics 2000;29 Suppl 1:S3-5.

Platt et al., "Mould Arthroplasty of the Knee, A Ten-Year Follow-up Study," *The Journal of Bone and Joint Surgery* (British Volume), vol. 51-B, No. 1, pp. 76-87, Feb. 1969.

Potter, "Arthroplasty of the Knee with Tibial Metallic Implants of the McKeever and MacIntosh Design," *The Surgical Clinics of North America*, vol. 49, No. 4, pp. 903-915, Aug. 1969.

Radermacher et al., "Computer Assisted Orthopaedic Surgery with Image Based Individual Templates," *Clinical Orthopaedics and Related Research*, vol. 354, pp. 28-38, Sep. 1998.

Rohlfing et al., "Chapter 11 *Quo Vadis*, Atlas-Based Segmentation?", in Handbook of Biomedical Image Analysis vol. III: Registration Models 435, 435-486 (Jasjit S. Suri et al. eds., Kluwer Academic/Plenum Publishers, NY 2005).

Rosset et al., "General Consumer Communication Tools for Improved Image Management and Communication in Medicine," Journal Digital Imaging, 2005;18(4):270-9.

Shakespeare D., "Conventional Instruments in Total Knee Replacement: What Should We Do With Them?" Knee. 2006;13(1):1-6.

Shepstone et al., "The shape of the Distal Femur: A Palaeopathological Comparison of Eburnated and Non-Eburnated Femora," Ann. Rheum Dis. 1999, 58:72-8.

Shirley et al., *Realistic Ray Tracing, Second Edition*, AK Peters, Natick, MA, 7 pages (Table of Contents), 2003.

Siston et al., "The Variability of Femoral Rotational Alignment in Total Knee Arthroplasty," Journal Bone Joint Surg Am. 2005;87(10):2276-80.

Siston et al., "Averaging Different Alignment Axes Improves Femoral Rotational Alignment in Computer-Navigated Total Knee Arthroplasty," Journal Bone Joint Surg Am. 2008;90(10):2098-104.

Soudan et al., "Methods, Difficulties and Inaccuracies in the Study of Human Joint Kinematics and Pathokinematics by the Instant axis Concept. Example: The Knee Joint," Journal Biomech. 1979;12(1):27-33.

Spencer et al., "Initial Experience with Custom-Fit Total Knee Replacement: Intra-operative Events and Long-Leg Coronal alignment," International Orthopaedics (SICOT), 2009:In Press.

(56) References Cited

OTHER PUBLICATIONS

Strothotte et al., Non-Photorealistic Computer Graphics—Modeling, Rendering, and Animation, Morgan Kaufmann Publishers, San Francisco, CA, 9 pages (Table of Contents), 2002.
Stulberg et al., "Computer- and Robot-Assisted Orthopaedic Surgery", Computer-Integrated Surgery Technology and Clinical Applications, edited by Taylor et al., Massachusetts Institute of Technology, Chapter 27, pp. 373-378, 1996.
Teeny et al., "Primary Total Knee Arthroplasty in Patients with Severe Varus Deformity. A Comparative Study," Clin Orthop Relat Res. 1991(273):19-31.
Vandeberg et al., "Assessment of Knee Cartilage in Cadavers with Dual-Detector Spiral CT Arthrography and MR Imaging," *Radiology*, vol. 222, No. 2, pp. 430-436, Feb. 2002.
Wright Medical Technology, Inc., "Prophecy Pre-Operative Navigation Guides Surgical Technique," 2009.
Wikipedia, the Free Encyclopedia, "CNC," (date unknown) located at http://en.wikipedia.org/wiki/CNC>, 6 pages, last visited on Apr. 12, 2007.
Amendment Under 37 C.F.R. 1.312, U.S. Appl. No. 13/374,960, filed May 7, 2013, 6 pages.
Non-Final Office Action, U.S. Appl. No. 12/390,667, mailed May 8, 2013, 20 pages.
Non-Final Office Action, U.S. Appl. No. 12/505,056, mailed Jun. 28, 2013, 7 pages.
Non-Final Office Action, U.S. Appl. No. 12/636,939, mailed Apr. 25, 2013, 16 pages.
Non-Final Office Action, U.S. Appl. No. 12/760,388, mailed Jun. 20, 2013, 54 pages.
Non-Final Office Action, U.S. Appl. No. 13/723,904, mailed Aug. 9, 2013, 6 pages.
Notice of Allowance, Design U.S. Appl. No. 29/394,882, mailed May 24, 2013, 16 pages.
Notice of Allowance, U.S. Appl. No. 12/563,809, mailed May 28, 2013, 11 pages.
Notice of Allowance, U.S. Appl. No. 13/086,275, mailed Aug. 27, 2013, 31 pages.
Notice of Allowance, U.S. Appl. No. 13/374,960, mailed May 6, 2013, 20 pages.
Preliminary Amendment, U.S. Appl. No. 13/731,697, filed May 10, 2013, 6 pages.
Response to Final Office Action, U.S. Appl. No. 12/563,809, filed May 6, 2013, 15 pages.
Response to Final Office Action, U.S. Appl. No. 12/636,939, filed Apr. 8, 2013, 10 pages.
Response to Non-Final Office Action, U.S. Appl. No. 13/086,275, filed May 7, 2013, 11 pages.
Response to Non-Final Office Action, U.S. Appl. No. 12/546,545, filed Jul. 15, 2013, 14 pages.
Response to Non-Final Office Action, U.S. Appl. No. 12/636,939, filed Jul. 16, 2013, 15 pages.
Response to Non-Final Office Action, U.S. Appl. No. 12/390,667, filed Aug. 7, 2013, 22 pages.
Response to Non-Final Office Action, U.S. Appl. No. 12/760,388, filed Sep. 12, 2013, 15 pages.
Response to Non-Final Office Action, U.S. Appl. No. 12/505,056, filed Oct. 9, 2013, 17 pages.
Response to Restriction Requirement, U.S. Appl. No. 12/760,388, filed Apr. 5, 2013, 7 pages.
U.S. Appl. No. 13/923,093, filed Jun. 20, 2013, Park.
U.S. Appl. No. 13/960,498, filed Aug. 6, 2013, Song.
U.S. Appl. No. 14/011,998, filed Aug. 28, 2013, Park et al.
U.S. Appl. No. 13/749,095, filed Jan. 24, 2013, Song.
Final Office Action, U.S. Appl. No. 11/641,569, dated Nov. 29, 2013, 20 pages.
Final Office Action, U.S. Appl. No. 12/505,056, dated Dec. 30, 2013, 48 pages.
Final Office Action, U.S. Appl. No. 13/723,904, dated Dec. 24, 2013, 10 pages.
Japanese Office Action, JP Application No. 2011-507530, dated Dec. 17, 2013, 8 pages.
Non-Final Office Action, U.S. Appl. No. 11/946,002, dated Feb. 6, 2014, 46 pages.
Non-Final Office Action, U.S. Appl. No. 13/730,467, dated Jan. 15, 2014, 8 pages.
Notice of Allowance, U.S. Appl. No. 11/641,569, dated Feb. 5, 2014, 11 pages.
Notice of Allowance, U.S. Appl. No. 12/390,667, dated Jan. 17, 2014, 9 pages.
Notice of Allowance, U.S. Appl. No. 12/546,545, dated Dec. 26, 2013, 9 pages.
Notice of Allowance, U.S. Appl. No. 12/760,388, dated Jan. 22, 2014, 13 pages.
Response to Final Office Action, U.S. Appl. No. 11/641,569, dated Jan. 29, 2014, 10 pages.
Response to Final Office Action, U.S. Appl. No. 12/390,667, dated Dec. 23, 2013, 5 pages.
Response to Final Office Action, U.S. Appl. No. 12/546,545, dated Dec. 9, 2013, 8 pages.
Response to Non-Final Office Action, U.S. Appl. No. 11/946,002, filed Dec. 6, 2013, 18 pages.
Response to Non-Final Office Action, U.S. Appl. No. 13/730,608, dated Jan. 7, 2014, 16 pages.
Response to Non-Final Office Action, U.S. Appl. No. 11/656,323, dated Jan. 17, 2014, 10 pages.
Response to Non-Final Office Action, U.S. Appl. No. 11/642,385, dated Feb. 24, 2014, 16 pages.
Siemens MAGNETOM Sonata 1.5T Technical Specifications, pp. 1-4, accessed online Jan. 28, 2014.

* cited by examiner

TOTAL JOINT ARTHROPLASTY SYSTEM

FIELD OF THE INVENTION

This invention relates to fabricating a value added medical device for patient-specific, total joint arthroplasty (TJA) procedures. More specifically, the invention relates to a system for producing a value added medical device or instrument (collectively referred to as a "medical device" herein), based on computer tomography (CT) or other imaging of a region of the body adjacent to a selected joint.

BACKGROUND OF THE INVENTION

Surgeons are generally dexterous and highly trained to achieve a standardized level of surgical skill. However, surgeons have limitations, including a lack of micron-level geometric accuracy. For example, a surgeon cannot place an instrument at an exact, numerically defined location (within, say, 100 µm) relative to a patient's body part and then move the instrument through a defined trajectory. Many surgeons are unable to exert a precise, predefined force in a selected direction. Furthermore, a surgeon may have small hand tremors that limit his/her ability to operate on very small and delicate structures. Unfortunately, many of these limitations affect the outcome of certain surgical procedures, especially in cases where micron-level geometric accuracy is required. For example, the three-dimensional locations and directions of basic procedures used to modify a bone (including drilling, cutting, and reaming) determine the alignment and fit of the implant(s). These factors directly influence these functional outcomes.

Recently, to assist surgeons in overcoming these limitations, computer-assisted surgery (CAS) utilizing robotic- or image-guided technologies has been introduced into various medical fields. CAS, as a categorization or surgical technology, includes not only robotics but also image-guided surgical devices, surgical navigation systems, pre-operative planners, and surgical simulators.

A primary goal of CAS technologies is to integrate pre-operative planning with intra-operative performance. One of the most important steps in integrating pre-operative medical images directly into operating room procedures is registration of image and corresponding body part(s). Registration is a computational procedure that matches pre-operative images or planning information to the position of the patient on the operating room table. Rigid pins or other fiducial markers were used in early systems, such as in a robot-assisted system.

For robot-assisted total knee alignment (TKA) surgery, illustrated in FIG. 1, two spaced apart pins, 11A and 11B, are fixed to a target bone 12 before CT images are formed of the damaged bone region 14. The phrase "CT imaging" or "CT scanning" will refer herein to any suitable two- or three-dimensional imaging procedure, including computer tomography, and magnetic resonance imaging. The pins, 11A and 11B, are used to allow alignment of a three-dimensional (3-D) reconstruction of the patient bone 12. The intra-operative locations of the pins are used to relate the position of the patient's bone to a pre-operative plan, using a robot controller 14.

Based upon a converted CT scan image of the exposed bone(s) in the damaged bone region, the location and angular orientation of the femoral mechanical axis (FMA), femoral anatomical axis (FAA) and tibial mechanical axis (TMA) are also determined, and a pre-operative plan for orientation and movement of the milling machine 16 are determined in a coordinate system relative to the target bone 12, to mill the bone end according to a pre-programmed cutting file. After the registration process i.e., matching the CT image bone model with the target bone using the two pins, the robot assistant is activated, and the milling cutter attached to a robot arm mills the damaged bone region to create one (or preferably several) exposed planar surfaces (transverse, anterior, chamfer, etc.) to accept and mate with a femoral implant.

This method is accurate, to the extent that the ready-made implant device matches the patient's own bone surfaces, but requires at least two surgical operations (including incisions or cutting for each): a first operation for installation of a robotic calibration mechanism and a second operation for the final surgery to install the TKA device itself.

The second surgical operation is constrained by a tourniquet time limitation, which places a practical limit on a maximum cumulative time an open wound can be exposed (usually 90-120 min for TKA) without severe danger of infection. This is another disadvantage of robot-assisted surgery, which requires use of a registration process and of a bone location fixation process, both time consuming. As compared to robot-assisted surgery, a conventional manual TKA procedure is usually completed in no more than 30 minutes, despite a relatively high probability of misalignment.

Shape-based registration, illustrated in FIG. 2, is an alternative method as shown in the previous art for TKA and THA that has been developed recently and currently used in clinical trials. A patent's damaged bone 21D is exposed, in a first surgical operation. A location coordinate sensor 22 is placed in contact with the damaged bone surface 21 at each of a a selected sequence of spaced apart locations, and the coordinates of each such surface point are received by a location coordinate processor 23 for subsequent processing. The processor 23 provides an approximate equation for the surface of the damaged bone region 21D. At least 15 surface coordinate triples are selected and digitized on the actual bone surface, and the data are analyzed and processed to match, as closely as practicable, the CT scan image data, using interpolation, extrapolation and other suitable mathematical approximations. When a matching relation is found, optical or other sensors track and guide a tracking device to provide a surgeon with the location and angular orientation information needed to identify a suitable implant device. For a TKA procedure, the image formation system guides and locates the tracking device to provide location and orientation of transverse, anterior chamfer cuts to fit the femoral implant.

Using the surface matching or registration technique illustrated in FIG. 2, the shapes of a model of the bone surface 21, generated from a pre-operative image, are matched to surface data points identified during the first incision or during surgery. Intra-operative surface data points can be specified by direct contact with percutaneous probes, from within the surgical exposure using ultrasonic or direct-contact optical probes, or from fluoroscopic radiographic images. Location tracking is a critical step in CAS. Tracking devices are attached to a target bone and to any tools to be used during the operation, such as drills, reamers, guides, or screwdrivers. Many common tracking devices use optical cameras and infrared light emitting diodes. These optical sensors are easy to set up, very accurate, have fast sensing rates of up to 100 measurements per second, and can track multiple tools simultaneously. A disadvantage of the devices illustrated in FIGS. 1 and 2 is that they require additional surgical time, require a direct line of sight to perform the procedure, require special training of surgeon and staff, require maintenance and frequent calibration of the robotic mechanism(s), and can be very expensive, depending on the required level of accuracy.

Other tracking technologies use acoustic or magnetic sensors that create an electromagnetic field around the surgical site that is altered as instruments move within the field. Such devices do not require a direct line of sight, but the devices may be less accurate, cannot be used with metallic tools, and have difficulties tracking multiple tools simultaneously. One major benefit of either of these tracking methods is a reduction in radiation, due to elimination of the need for intraoperative fluoroscopy or radiography to check component position.

The systems described in the preceding discussion often suffer from a lack of readiness for the operating room and do not always address practical considerations. Many systems introduce additional capital equipment, equipment maintenance and operative steps into the surgical procedures that prolong the surgery and require significant training. Further, most of the systems do not address the issues of sterility and safety, and unwanted motion of the body part(s) to be operated upon. Most systems require input from the surgeon in order to specify data or alter program flow. Many systems rely on a non-sterile assistant to enter data, using a keyboard, mouse or pen, but this is inefficient and risks miscommunication. A sterilized or draped input device, introduced into the surgical operating theater, may be difficult to use, may be distracting for the surgeon, requires the splitting of the surgeon's attention between the display screen in one location and the surgical tool in another, and requires removal of the tool from the surgical site for use elsewhere as an input device.

What is needed is a system that requires only one surgical procedure (defined as requiring at least one incision or cutting operation), employs a pre-operative scanning procedure that provides micron level accuracy, is flexible enough to account for certain tolerances relative to an idealized fit, and provides a fabricated, patient-specific cutting jig and a patient-specific (optional) implant device whose components can be aligned and altered according to the body part(s) involved.

SUMMARY OF THE INVENTION

The needs discussed in the preceding paragraph are met by the invention, which uses pre-operative scanning and construction of a geometric model of the target body part surface, re-operative fabrication of a patient-specific cutting jig and a patient-specific (optional) implant device, which may have one or more than one component, monitoring and correction of the jig and/or implant device, vis-a-vis the target body part, and relies on a single surgical procedure to remove a selected part of a damaged bone and to implant and initially test an implant device (optional) in vivo.

One feature of the invention is use of an image-based surgical system in total joint arthroplasty, such as total hip arthroplasty (THA), total knee arthroplasty (TKA), total elbow arthroplasty (TEA), spinal surgery, etc. The system software receives or provides geometrical information on the damaged bone, captured in CT or another suitable imaging format, and converts his information into a three-dimensional (3D) model of the bone surfaces during the computer-aided pre-operative planning. The converted 3-D model includes the information on corresponding bone dimensions along with the uncertainties associated with CT scanning and conversion errors. The system displays all the pertinent information on the damaged bones on the screen. The system provides a surgeon with improved visualization of the relationship between the damaged bone and the cutting jig or implant device, including but not limited to accurate alignment of the device, by accurately superimposing representations of a cutting jig and/or an implant device being used in the surgical field over the images of the bone.

Another feature of the invention is that, once the planning is complete, the system software prepares and provides a computer file to direct rapid production machines, such as a computer numerical control (CNC) machine, a stereo-lithograph (SLA) machine, etc, to fabricate a cutting jig and/or an implant device (optional), which may be disposable (replaceable) or non-disposable (recyclable). The value added cutting jig and/or implant device is made of any bio-compatible material and works with a manual and/or automated instrument to transfer joint planning information between a computer-aided pre-operative planning phase and the actual surgical procedure. During surgery, the cutting jig is employed to guide critical cuts and shaping of the bone, such as drilling, reaming, sawing, etc. The cutting jig and/or implant device (optional) includes a surface profile that matches the bone surfaces in vivo.

With reference to the cutting jig surface profile, guiding holes for drilling and inspection, a slot feature for a sawing process, and bushing features for reaming and drilling are fabricated. Alternatively, the surface profile can be created with reference to guiding holes, slots and bushings.

A related feature of the invention is that the system software performs virtual surface mapping techniques with respect to the 3D model based on CT scan images, including point-to-point mapping, surface normal vector mapping, and surface-to-surface mapping techniques. Depending on the application one or a combination of mapping techniques can be employed.

Another feature of invention is that the system software includes transferring of all pre-operative planning data and related computer files to a production floor model through a selected communication system (e-mail, file transfer protocol, web-browser, LAN, fiber optic cable, wireless, etc. and/or manual transfer).

Another feature of the invention is that, upon receiving the data from a remote planning station, the system software automatically executes and provides information pertinent to the rapid production and inspection processes. A quality control procedure includes monitoring and verification of 1) the surface profile of a cutting jig and of an (optional) surgical implant device compared to the 3-D profile of the bone virtual surface from the CT image and 2) translation and angular positioning of the fabricated features such as drilling holes, slots and bushings. Later, the jig and the (optional) implant device are cleaned, sterilized (optional), packaged and delivered to the surgical operating theater.

These features and advantages of the present invention are embodied in an improved system for assisting a surgeon in using a surgical tool to provide accurate cutting, implant positioning and alignment with respect to one or more body parts. The system uses a computer-aided calibration process involving a surface matching of the cutting jig and/or implant device to the bone surface(s). Because the cutting jig and/or implant device is fabricated using CT scan image data, there is no need for use of a registration process, expensive tracking systems or robotic systems in an operating room, or for use of two or more surgical procedures. The invention is designed to work in conjunction with any manual standard TJA instrumentation, and thus minimizes additional expenditures for capital equipment purchases. Furthermore, there is no increase in surgical time, and the cutting jig and/or implant device can provide a reduction in surgical time.

DETAILED DESCRIPTION OF THE INVENTION

1) System Architecture

In a preferred embodiment, the invention provides accurate positioning and alignment of an orthopedic implant without a significant increase in surgical time or capital equipment cost. Also, during the actual surgery, the system does not require use of registration, image matching or location tracking, which distinguishes the invention from other image-based systems.

FIGS. 3A, 3B, 3C and 3D illustrate some features of the invention. A damaged region 31D of a target bone 31 undergoes CT scan in FIG. 3A. Pre-operative planning is performed, using a computer and a CT image scanner 32, to construct a model of bone surfaces adjacent to the damaged region 31D, with an associated inaccuracy of no more than 90 μm. Based on the accumulated planning data, a production file is created to receive the CT image data and to fabricate a jig or cutting block and, optionally, an implant device. The production file and the planning information are sent to the production floor for fabrication of a patient-specific jig and a corresponding implant device (patient-specific or off-the-shelf).

Figure 1:
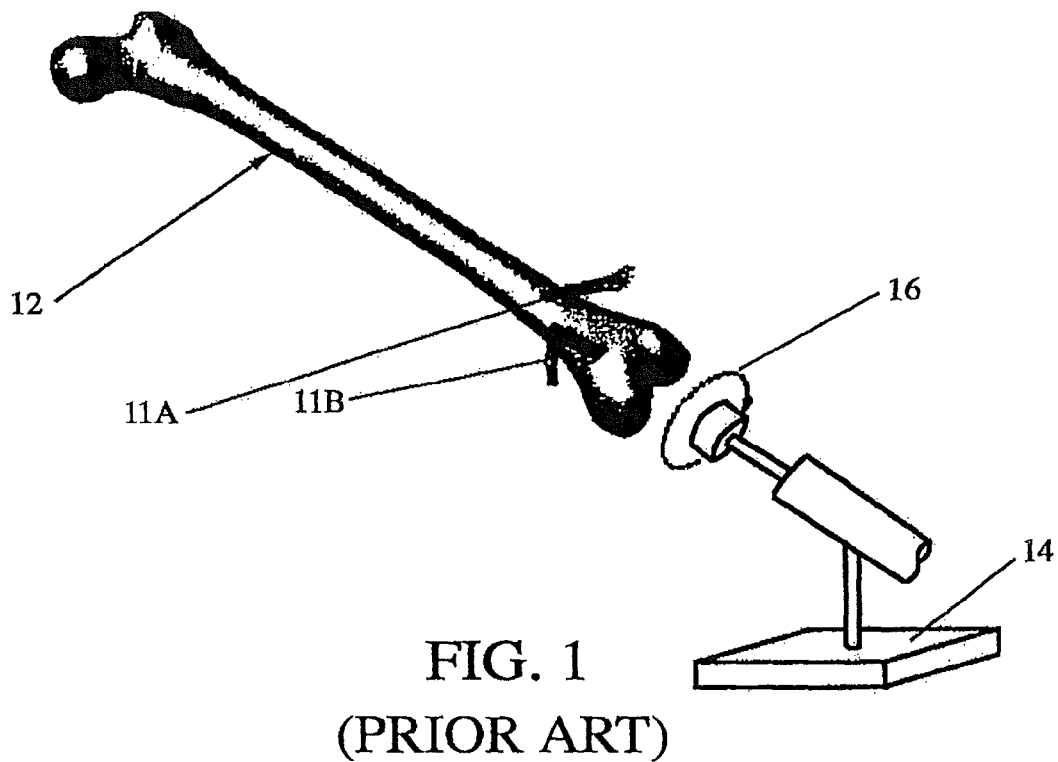
FIG. 1 illustrates robot-assisted total knee arthroplasty (TKA).
Figure 2:
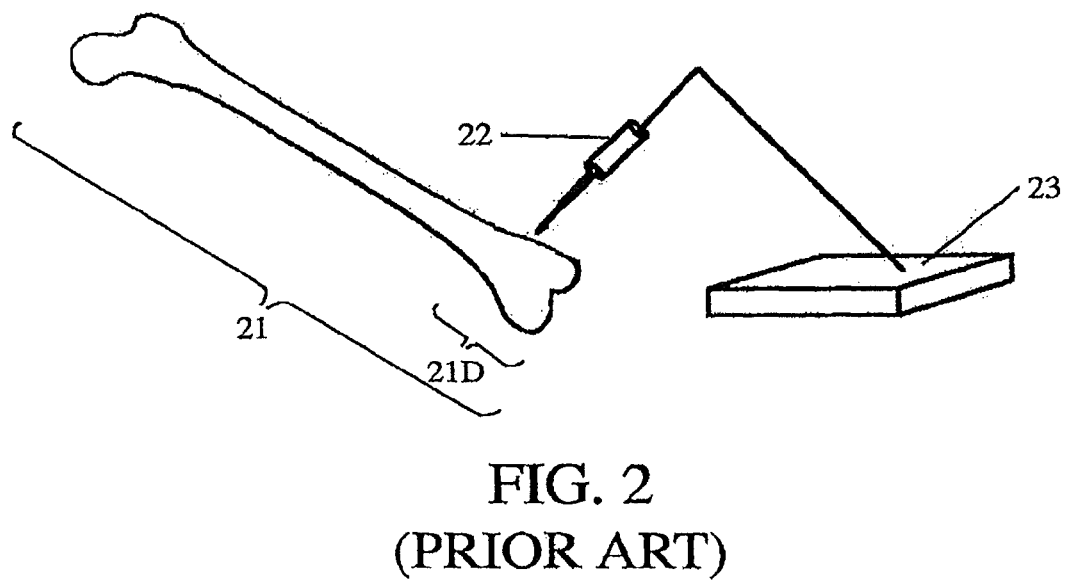
FIG. 2 illustrates shape-based registration in TKA.
Figure 3A:
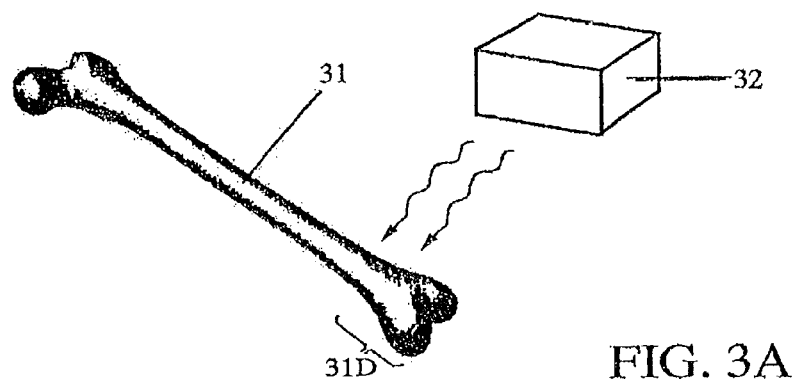
FIG. 3A illustrates a damaged region of a target bone undergoing CT scan.
Figure 3B:
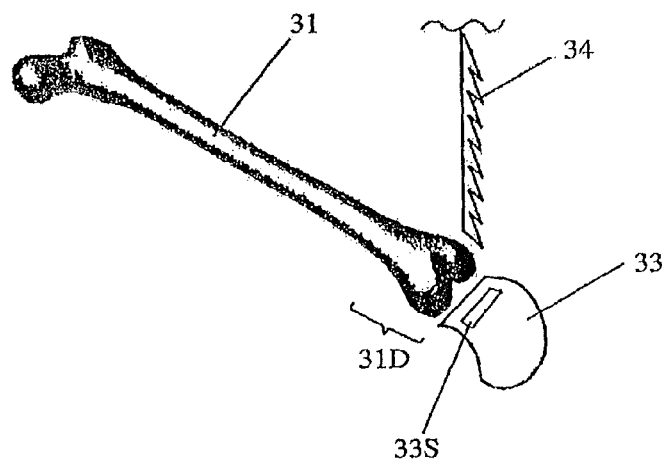
FIG. 3B illustrates the target bone as shown in FIG. 3A with a jig having a transversely oriented slot or aperture to accept a cutting instrument, such as a saw blade.
Figure 3C:
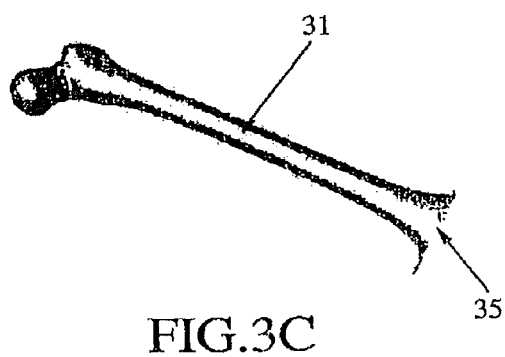
FIG. 3C illustrates the target bone as shown in FIG. 3A with the damaged region having been removed.
Figure 3D:
FIG. 3D illustrates a fabricated implant device.

In FIG. 3B, a jig 33 is fabricated to seat against the femur (or against the tibia, for tibia processing) and has a transversely oriented slot or aperture 33S that accepts and provides a guide for a cutting instrument 34, such as a reciprocating saw blade. After incision in the patient's body, the cutting instrument 34 would be placed in and aligned with the slot 33S so that, when the cutting instrument is activated and the femur (or tibia) is exposed, a distal end portion of the femur (or proximal end portion of the tibia) can be removed to provide a planar exposed surface 35, as illustrated in FIG. 3C.

Note that no incision into or cutting of the patient's body has yet occurred; the jig 33 and slot 33S are designed and fabricated using primarily the information obtained from the CT image scan. An implant device 36, illustrated in FIG. 3D and having a planar surface, is optionally fabricated from the CT scan information, without incision into or cutting of the patient's body.

The fabricated jig 33 and optional implant device 36 are delivered to a surgical operating theater, and the patient's body is cut open to expose at least the distal end of the femur 31 and the proximal end of the tibia in the damaged bone region 31D. The jig 33 and slot 33S are positioned, and a member of the surgical team removes a portion of the distal end of the femur 31 (and, similarly, removes a portion of the proximal end of the tibia) to provide an exposed and aligned planar surface 35 (and, similarly, to provide an exposed and aligned planar surface of the tibia). The femur jig 33 is then removed, and a corresponding planar surface of the femur implant device 36 is optionally attached to the exposed planar surface of the femur distal. This attachment may be done using one, two, three or more attachment mechanisms, such as bolts, screws or nails, that attach the femur implant device 36 to the remainder of the distal end of the femur, at the femur planar surface 35. In a similar manner, a tibia implant device is attached to the remainder of the proximal end of the tibia at the tibia planar surface.

During the surgery, the custom mating between the jig 33 and the remainder of the target bone (femur and/or tibia) at the exposed planar surface ensures a precise fit (location and alignment, drilling holes and a slot 33S) for surgeons in performing the joint repair/replacement process with any manual standard instrumentation.

Figure 4A:
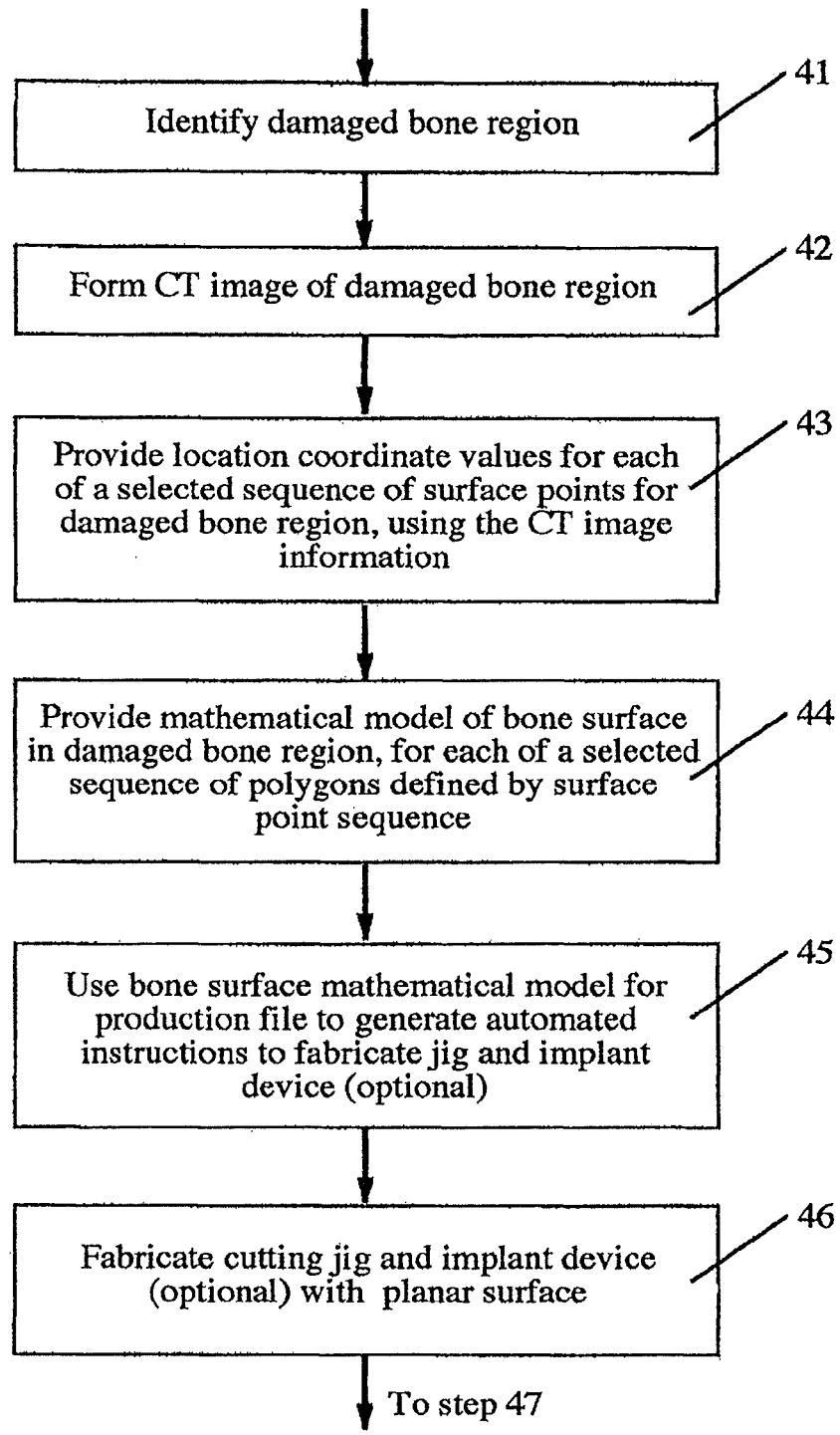
FIGS. 4A/4B are a flow chart of a procedure for practicing the invention.
Figure 4B:
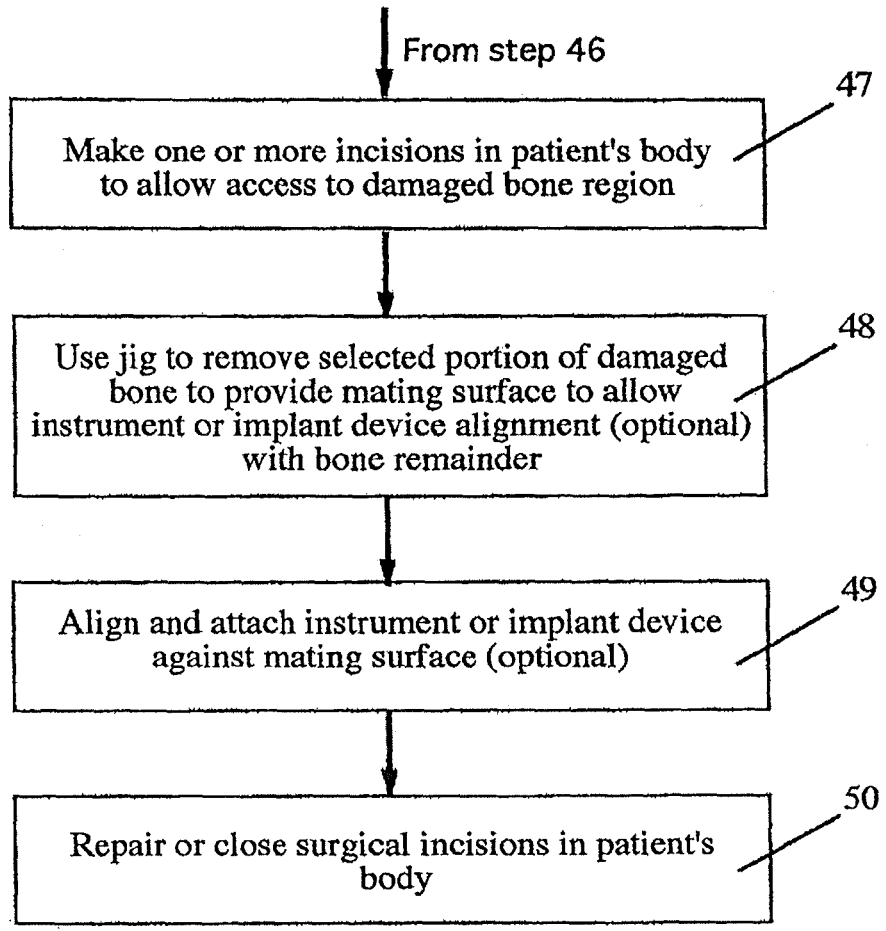

FIGS. 4A/4B are a flow chart for practicing the invention. In step 41, a damaged region of a bone, or of one or more adjacent bones, is optionally identified. In step 42, a CT image is formed of the damaged bone region and, preferably, of all portions of each bone involved in the damaged region (e.g., proximal end of the femur and/or distal end of the tibia). For example, if a femur-tibia connection at a knee is damaged, a CT image of the full length of the femur and of the full length of the tibia are preferably formed, including the ends of these bones that are not involved in the damaged bone region. In step 43, location coordinate values of each of a sequence of spaced apart surface points on each bone in the damaged bone region are determined from the CT image. Optionally, these location coordinates are referenced to an absolute coordinate system associated with the damaged bone region.

In step 44, a model of a bone surface in the damaged bone region is estimated or computed, using a mathematical method described herein or another appropriate method. Optionally, the surface points are used to subdivide the bone surface in the damaged bone region into a sequence of polygons P, preferably triangles and/or quadrilaterals, as part of the surface modeling process. At least three approaches are available here.

In a first approach, a mathematical model of the surface is developed that matches, as closely as possible, the coordinate values $(x_n, y_n, z_n)$ of each of the sequence of surface location points provided by the CT image. Here, the bone surface may be modeled within each of the sequence of polygons P, and the sequence of approximations can be treated collectively for the bone surface as a whole; or the bone surface may be modeled in the large by a single polynomial, trigonometric series or other function set in appropriate location coordinates, such as Cartesian coordinates (x,y,z).

In a second approach, a surface normal at a selected point within each of the sequence of polygons P is measured or otherwise provided, using the CT image information, and a surface portion within that polygon is determined for which the surface normal matches, as closely as possible, the CT image-provided surface normal at the selected point. In a third approach, use of surface point locations and surface normal vectors are combined.

In step 45, the mathematical model determined for the bone surface in the damaged bone region is used, as part of a production file, to generate automated instructions for fabricating a cutting jig and an implant device (optional) for each of the femur and the tibia. In step 46, the cutting jig and the implant device (optional) are fabricated, using the production file cutting jig preferably includes a planar surface to allow the implant device to mate with and align with the bone.

In step 47, one or more incisions is made on the patient's body to expose the damaged bone region and to allow access to the damaged bone region. The cutting jig is used to remove a selected end portion of the bone and to provide an exposed planar surface of the bone remainder.

In step 48, a selected portion of the damaged bone is removed, using the cutting jig, to provide a planar surface against which an implant device will be (optionally) fitted.

In step 49, the implant device is optionally fitted to, and secured against, the planar surface of the bone remainder, and alignment of the implant device with one or more bone axes and implant device attachment is implemented. In step 50, the surgical incisions in the patient's body are repaired; the patient's body is "sewn up" (once). Only one surgical procedure, with its concomitant incisions and cutting, is required here, and this surgical procedure requires an estimated 20-25 minutes to complete, including bone end remainder and implant device alignment and attachment.

The following is a more detailed discussion of practice of the invention for TJA, where the damaged bone region is a patent's knee.

Figure 5:
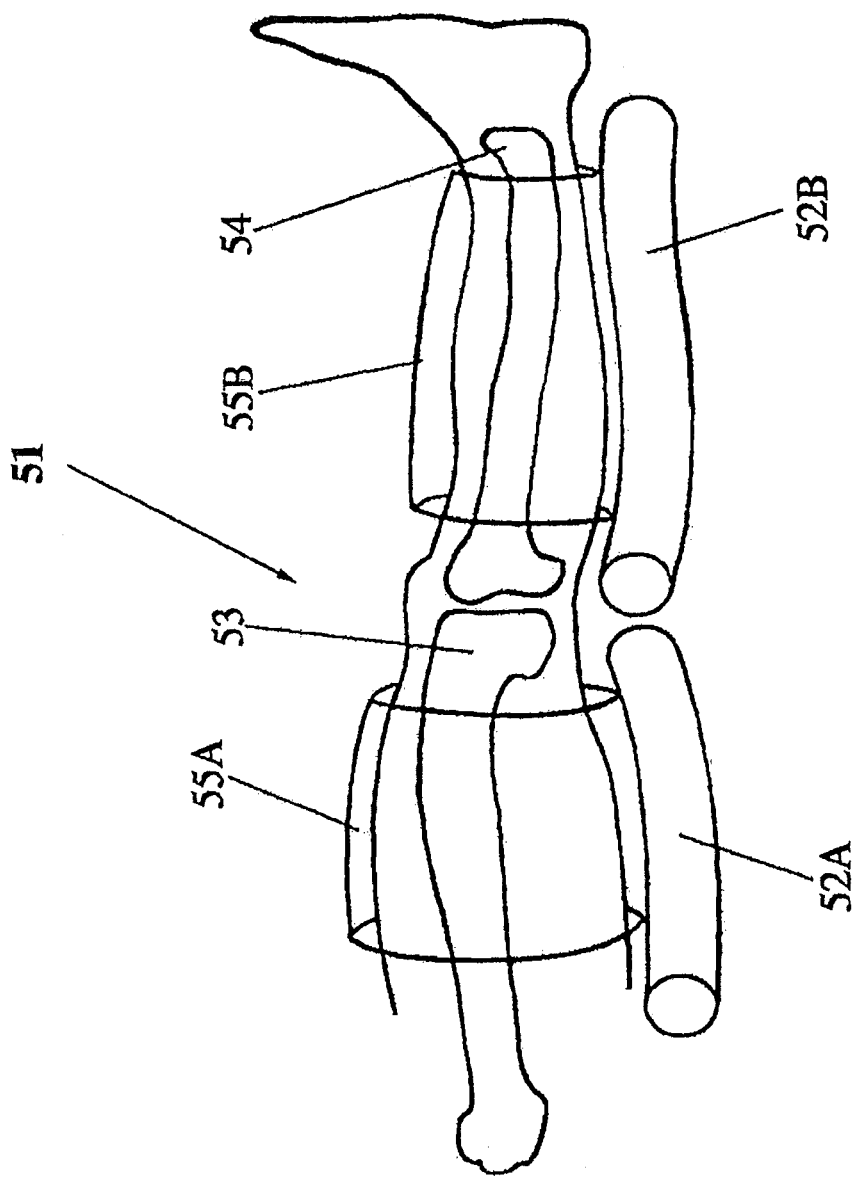
FIG. 5 illustrates a non-invasive bone positioning device used in pre-operative planning according to the invention.
Figures 6, 7:
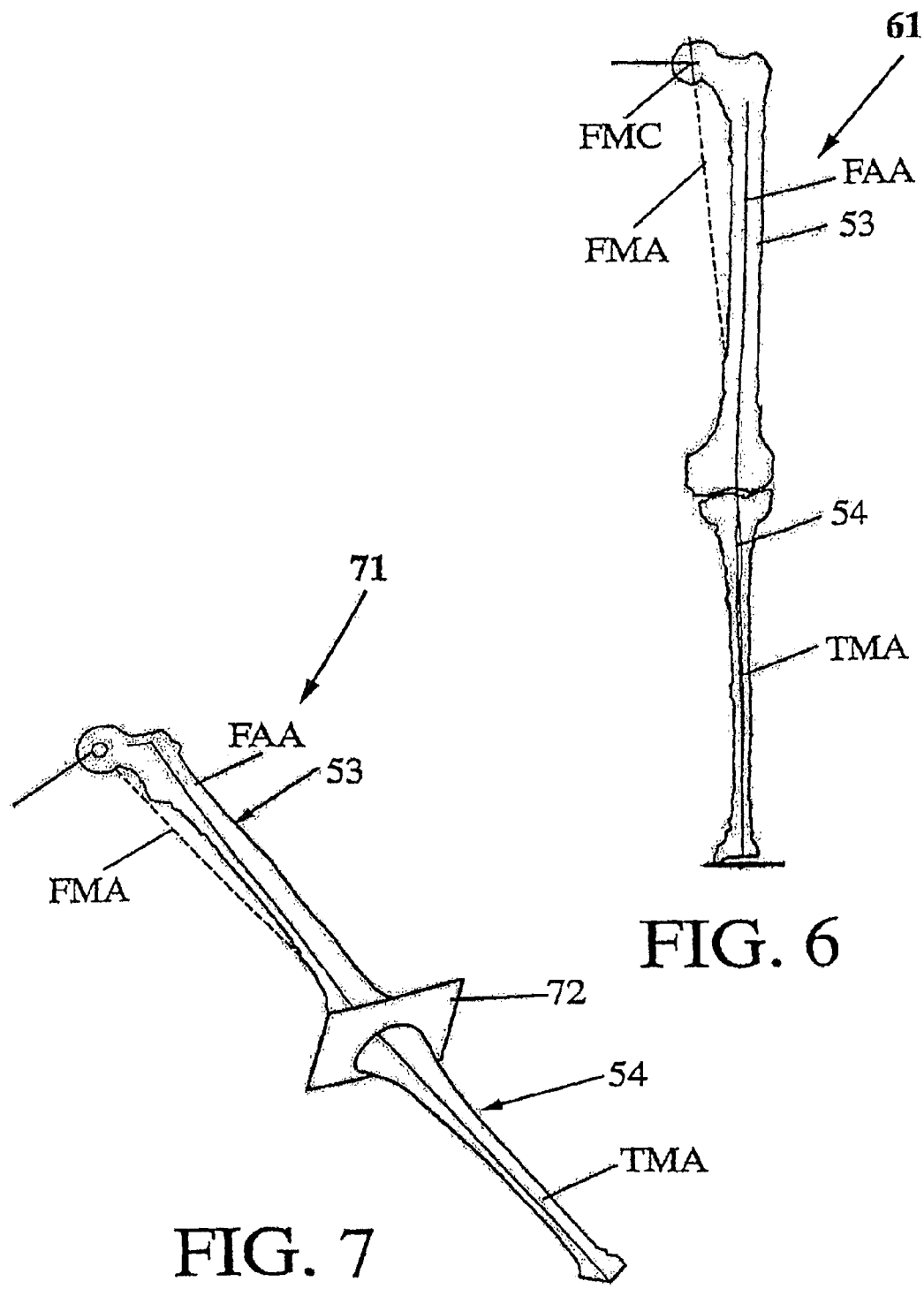
FIG. 6 illustrates three axes of interest on a femur and a tibia.
FIG. 7 illustrates pre-operative planning and measuring according to the invention.

Stage I:

A non-invasive bone fixturing device 51 is provided (not requiring cutting or piercing of the skin), including a system of rigid bars, 52A and 52B, strapped to and immobilizing the patient's femur 53 and tibia 54 by a plurality of elastic straps, 55A and 55B, as shown in FIG. 5. Optionally, the bone fixturing device 51 is also used as a reference frame. The damaged knee (or other joint) of the patient is CT scanned and processed into a computer file, using a selected reference frame. With the exception of severely abnormal or fractured knee joints, the CT scan concentrates on pertinent areas, in and around the damaged bone region, that will assist in determining the femoral mechanical axis (FMA), femoral mechanical, center (FMC), femoral anatomical axis (FAA) and tibial mechanical axis (TMA), as shown in FIGS. 5 and 6. The CT image data, including data conversion into a 3-D geometric format, are received by a computer, and the system automatically performs the following: (1) A 3D conversion algorithm is utilized to provide 3D graphical representation of the knee components, where the algorithm provides optimal graphical representation for the knee implants' planning process as well as downstream production applications; and (2) The system software analyzes bone motion detection and re-configuration algorithms. If bone motion is detected, the system analyzes and re-configures the bones (here, femur 53 and tibia 54) with respect to the bone positions. If too much movement is detected, the system recommends re-scanning the knee to provide a new image.

Stage II:

The 2D and 3D models of the knee from Stage I are viewable on the preoperative planning system PC display as well as a library LINK of the femoral and tibial knee implant components. The library includes 3D models of various size implants and other ancillary parts. The names of the implant manufacturers and manufacturer's surgical criteria and optimum alignment conditions for implant installation will also be available. As an example, using the system to determine the FMA, the surgeon may execute the following sequence: (1) select the center of the femoral head with an icon; (2) select the center of the knee (other end of the femur) with another icon; and (3) connect the two icons with a straight line. This defines an FMA, one of the axes, as illustrated in FIGS. 5, 6 and 7. If the surgeon has a preferred way of determining the FMA, the surgeon has the flexibility to use any desired graphical method. For ascertaining the FAA and the TMA, also shown in FIG. 7, similar techniques are implemented. Similar to commercially available graphic software, the preoperative planning system includes capabilities for enlargement, shrinking, panning, zooming, rotating, etc. As shown in FIG. 7, a plane 72, perpendicular to FMA, represents a transverse cut of the distal femur 53 (and of the proximal tibia 54); this information is used to create a slot for transverse cutting during the actual surgery.

The system allows a surgeon to perform the following: (1) check the results of the pre-operative planning to avoid or minimize the consequences of mistakes; and (2) simulate and recommend other available orthopedic theories, techniques and case studies, i.e., for bowed legs and fractured knees, which will be based on recent literature, surveys and widely accepted knee kinematics and alignment theories. This particular portion of the system is optional; the surgeon makes the final decision s in implant planning.

Figures 8A, 8B:
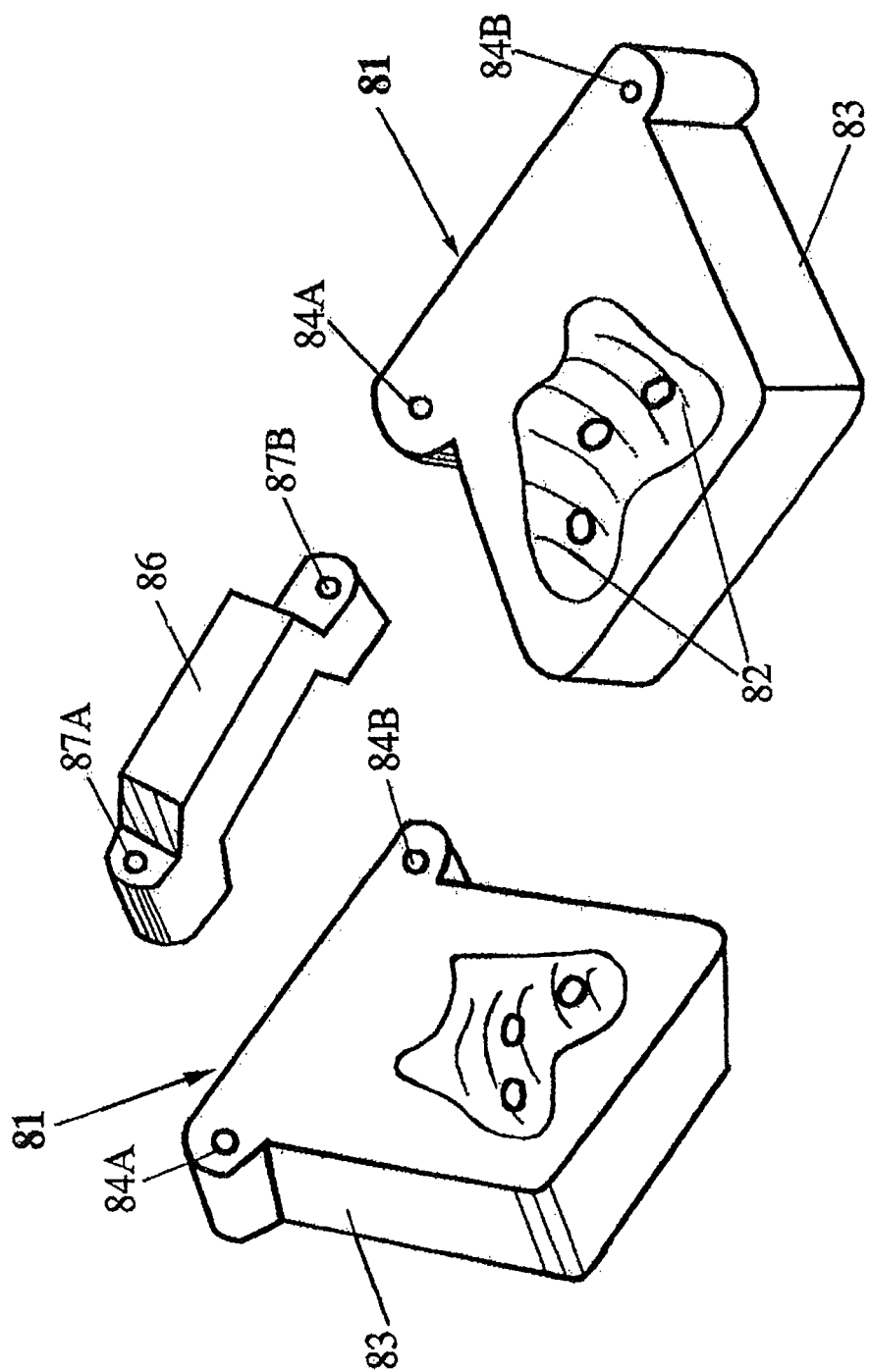
FIGS. 8A/8B/8C are schematic views of a surgical implant device for TKA, prepared according to the invention.

Stage III:

The system generates a production file, including a machining or fabrication file, based upon information of the planned position and alignment of the femoral and tibial components from the previous stage. This file is used to control a production machine that fabricates the patient-specific jigs for both femoral and tibial aspects of the knee. These unique jigs, an example of which is shown in FIGS. 8A/B/C, implement transfer and use of information between pre-operative planning and surgery and allow a member of the surgery team to provide a clean, precise slice and an exposed planar surface of the remainder of the bone. The production file creates one or more selected internal (mating) surfaces of the exterior surface profile for the damaged knee surface geometry, for accurate patient-specific mating between the jig and the remainder of the patient's distal femur. In addition, the production file creates a transversely oriented slot and cutting instrument guide for a transverse cutting process. These features are optionally created with respect to the intercondylar aperture (FAA) as a reference point. Accurate mating between the jig and the distal end of the femur ensures the accurate translation and angular position of the slot as planned in STAGE II. This provides the surgeon with access to a transverse cut on the distal femur, which establishes the correct alignments and provides reference planes for assembling manual instrumentation for the rest of the cuts required for knee implant installation.

Figure 8C:
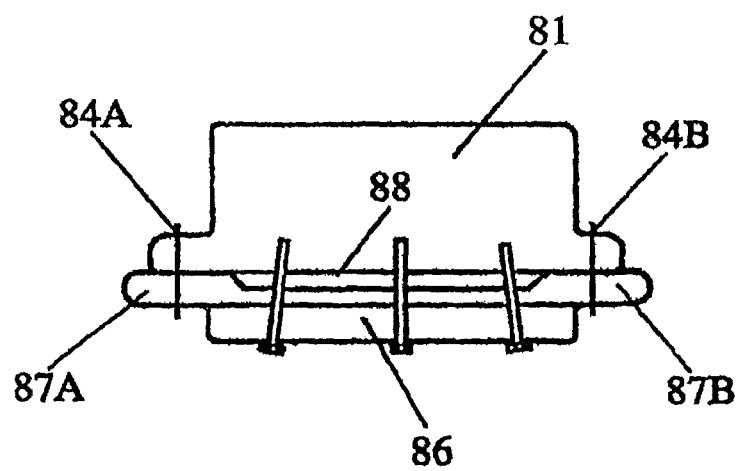

FIGS. 8A and 8B are perspective views of a cutting jig, 81 and 86, fabricated according to the invention. The model of the damaged bone region is used to define a selected region 82 to be removed from a block 83 of hardened material (preferably a bio-compatible plastic) that is a first component 81 of the cutting jig. The region 82 is selected so that the damaged bone region will fit snugly into the hollowed-out region in the block 83. First and second lateral projections, 84A and 84B, are provided on the block 83, with each projection having an aperture that is approximately perpendicular to an initial surface 83S of the block 83. A second component 86 of the cutting jig includes third and fourth projections, 87A and 87B, that mate with the respective first and second projections, 84A and 848, of the first component 81. Apertures in the third and fourth projections, 87A and 87B, mate with and are aligned with the apertures in the first and second projections, 84A and 84B, respectively. When the first jig component 81 is mated with the second jig component 86, a small, transversely oriented gap 88 is defined between the first and second jig components, into which a cutting instrument can be inserted to cut of and remove a damaged region of the bone, as illustrated in FIG. 8C. After a transverse cut is made, using the jig 81/86, a first aperture is formed in the remainder of the bone, along the bone longitudinal axis, and one or more additional apertures are formed, parallel to and spaced apart from the first aperture. These apertures are used to align an implant device with the bone remainder.

Figure 9:
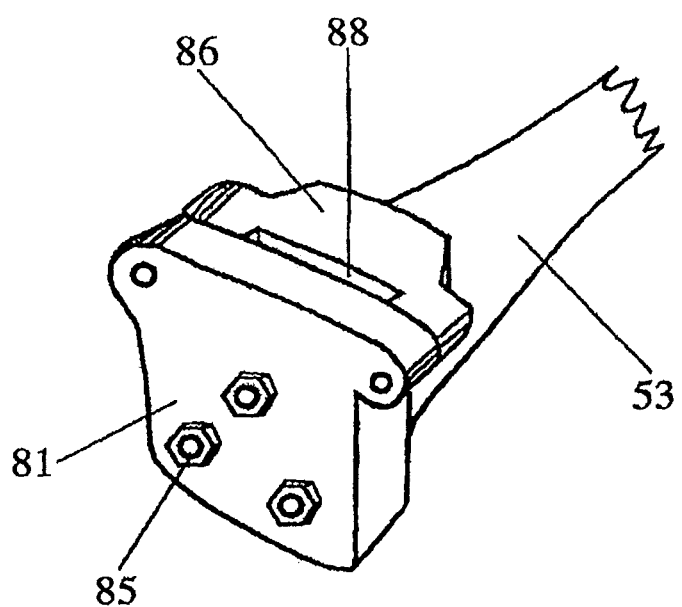
FIG. 9 is a schematic view of mating of a component of the implant device and a body part (femur) of the patient.

The system automatically determines the correct size of the jigs for the distal end of the femur and the proximal end of the tibia (53 and 54 in FIG. 5). The system includes an algorithm for determining optimum mating conditions through volume and tolerance/interference checks between the patient knee and the jigs. FIG. 9 illustrates how the virtual mating of the patient-specific jig components, 81 and 86, to the distal femur 53 are displayed on a PC screen. The system includes an algorithm that performs the following functions: (1) generation of efficient production processes; and (2) determination of production parameter conditions. In this stage, no surgeon or user intervention occurs, and the production file along with CT image file is transferred from the hospital planning station to a rapid production floor through a secure inter-net connection or other methods.

Stage IV:

The patient-specific jigs (optionally disposable) are fabricated with rapid production machines. The fabricated features are inspected through a quality control procedure. During the production process, reporting status and error conditions are critical. In order to achieve high quality surface mating, the accommodation of control modules that actively monitor and adjust the machining process should be considered. The system automatically executes and provides information pertinent to the production and inspection processes. The quality procedure involves monitoring and verification of (1) the profile surface of the jigs compared to the profile of the knee surface determined from the image and (2) translation and angular positioning of the machined features such as transverse and tibial cutting slots. Finally, the jigs are cleaned, sterilized (optional), labeled, packaged and delivered to the hospital. As yet, no cutting of the patient's body has occurred, Modeling of a Bone Surface Other inventions require so called shape-based registration that the shapes of the bone surface model generated from a pre-operative image are matched to surface data points collected during a first phase of surgery. This surface matching method requires finding a mapping relation (transformation matrix) between bone surface data points and the bone surface model. Therefore, the accuracy of registration process depends on the number of points and distance between each point. Once the mapping relation is found, the pre-operative plan can be performed based on the mapping relation during the surgery. The mapping relation between surface data points and the bone surface model from a pre-operative image can provide surgeons with the pre-operative image based planning information needed for a successful surgery. A key to the success of this method is determination of an accurate bone surface representation of a pre-operative image. The more accurate the bone surface model is, the more precise the position and alignment of the implant device.

This invention differs from other approaches in not requiring use of a registration process during actual surgery. The invention relies upon a virtual registration process for a bone surface mathematical model generated from a pre-operative, CT scanned image. In order to achieve this goal, the invention includes the interpolated deterministic data points as well as uncertainty associated with each point. This uncertainty information is critical for the production of surgical device (hardware) and surgical error analysis prior to surgery.

Several approaches can be used for virtual registration.

(1) Point-to-point mapping on the bone surface model. Virtual data points on the 3D CT bone surface are selected to accurately describe the distal femur and the proximal tibia in the damaged bone region. Based on the selected data points, virtual pins are introduced at selected surface points with corresponding coordinate values, such as (x,y,z), that are to be used to map the bone surface at these locations. The directions of all virtual pins are straight and may be parallel to, or transverse to, the femoral anatomical axis (FAA). No particular pin direction is required. A pin can point at each selected surface point in any direction, for example in a direction of a surface normal at that surface point. Once the pre-operative planning is completed, an implant device can be fabricated using available manufacturing techniques. The surgical hardware can be disposable or re-usable. During surgery, the implant device with pre-operative planning information, such as slot position and drilling hole locations, is placed on the distal femur. Custom mating between the surgical device and the distal (or proximal) bone surface ensures accurate mapping relation between the actual bone surface and the bone surface model. The more data points are selected, the more accurate surgical result is obtained.

(2) Surface normal vector mapping on the bone surface model. Sufficient virtual data points on the 3D CT image bone surface are selected to describe the geometry of the distal femur and the proximal tibia. Based on the selected data points, virtual pins and pin directions are introduced at the selected data points, with the direction of each virtual pin being normal to the surface at each selected point. The virtual pin directions are arbitrary, but a pin direction normal to the local surface is preferred. Once this pre-operative planning is completed, surgical device can be made using any available manufacturing techniques. The surgical hardware, including jig, can be disposable or re-usable. During surgery, the implant device (patient-specific or off-the-shelf), including pre-operative planning information, such as slot position, drilling hole locations is fabricated and placed on the distal femur. Custom mating between the implant device and the distal bone surface ensures accurate mapping relation between the actual bone surface and the bone surface model. A sufficient number of surface point locations and corresponding normal vector component values are determined (preferably five or more) to provide an accurate model of the bone surface.

(3) Local surface mapping on the bone surface model. Several local mating virtual areas on the 3D CT image bone surface are selected to describe a geometry of the distal femur and proximal tibia. The local surface-to-surface mapping is equivalent to case (2), surface normal vector mapping, but uses a significantly larger number of data points. Once this pre-operative planning is completed, surgical device can be made using any available manufacturing techniques. The surgical hardware can be disposable or re-usable. During surgery, the implant device with pre-operative planning information, such as slot position, drilling hole locations is placed on the distal femur. Custom mating between the implant device and the distal bone surface ensures accurate mapping relation between the actual bone surface and the bone surface model. Use of a local area surface mapping approach can significantly increase the accuracy and reliability of the surgery.

(4) Global surface mapping on the bone surface model. One global mating virtual area on the 3D CT image bone surface is determined to describe the geometry of the distal femur and proximal tibia. A global surface-to-surface mapping is employed, and this approach is equivalent to case (3), the local surface mapping on the bone surface model, with the increased surface contact areas. Once this pre-operative planning is completed, surgical device can be made using any available manufacturing techniques. The surgical hardware can be disposable or re-usable. During surgery, the implant device with pre-operative planning information, such as slot position, drilling hole locations is placed on the distal femur. Custom mating between the implant device and the distal bone surface ensures accurate mapping relation between the actual bone surface and the bone surface model.

Precise pre-operative planning is essential for a successful TJA. Several techniques of CT-based pre-operative planning have been developed. The system allows the surgeon to develop a plan of component placement in TJA. Surgeons can check the plan that they have made by referring to the geometric relationship with respect to the implant.

A repaired knee joint, or other joint, may fail prematurely, for any of several reasons. Instability of the implant device, due to kinematic misalignment, may cause such failure and may require performance of a revision TKA. This is a delicate surgical procedure in which additional bone loss, due to realignment, must be minimized. A revision TKA begins with removal of the original implant device and of any bone cement remaining between the implant device and the exposed bone surface. During pre-operative planning, a bone surface image can be formed and preserved, not including the bone cement and implant device surfaces. Based on this (preserved) image data, another patient-specific jig is fabricated with its own (corrected) cutting slot, using the techniques discussed for primary or original TKA. Because all bone surfaces are already shaped due to the earlier primary TKA procedure, use of a surface-to-surface mapping would be appropriate here.

Mathematical Details of Bone Surface Matching.

Figure 10A:
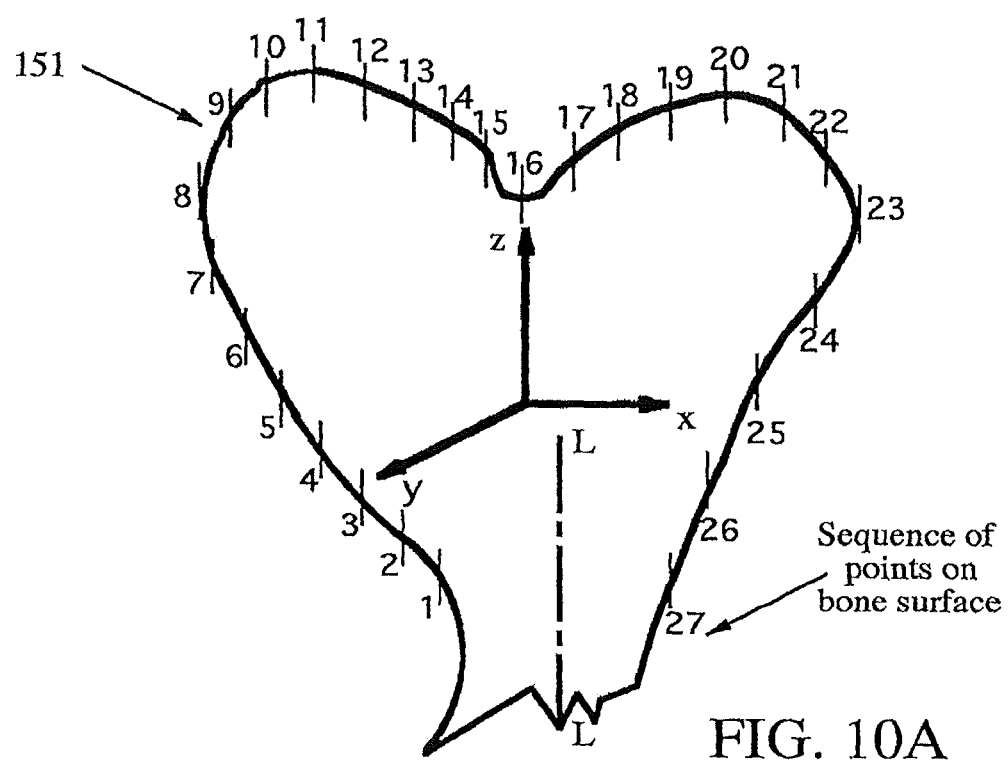
FIGS. 10A, 10B, 11 and 12 illustrate a procedure for estimating a local shape function for point-to-point matching on a surface.
Figure 10B:
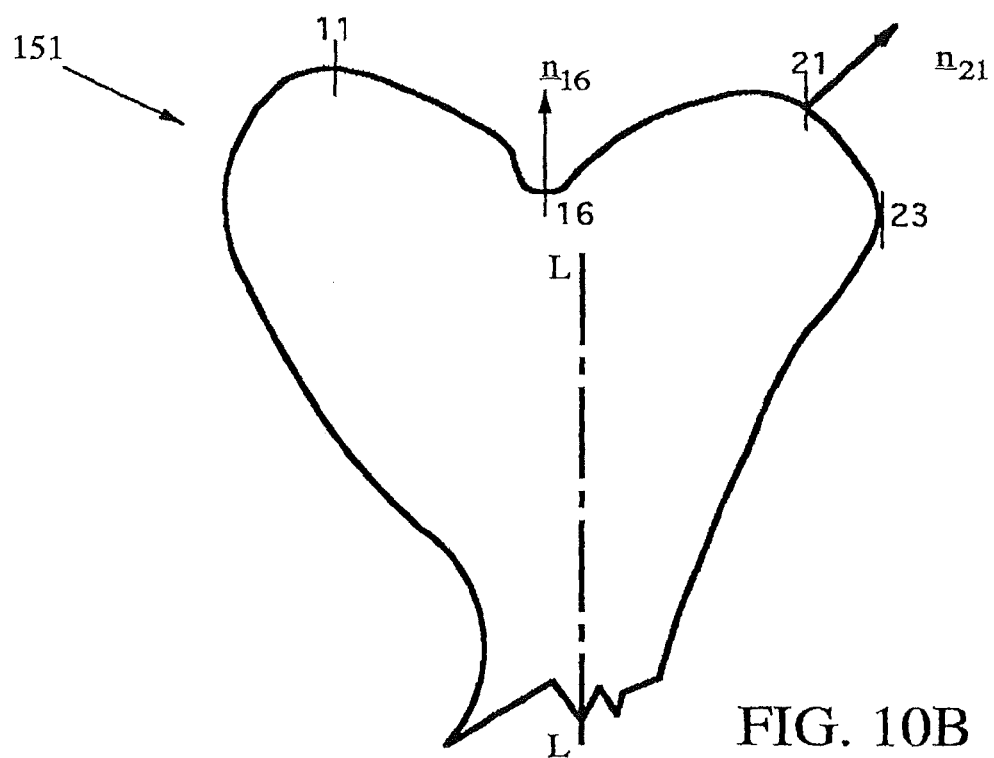

FIGS. 10A and 10B are views of a slice of an end of a bone 151, such as a femur or a tibia, that is analyzed using a CT scan to provide an estimate of a surface shape function $z=f_s(x,y)$ that accurately describes an end portion of the bone. An (x,y,z) Cartesian coordinate system is shown imposed on the bone 151, with the z-axis oriented approximately parallel to a longitudinal axis LL of the bone, and the slice optionally corresponds to a plane $a \cdot x + b \cdot y = $ constant; for convenience in notation, it may be assumed here that $a=0$. In FIG. 10A, a sequence of spaced apart points with coordinates $(x_n, y_n, z_n)$ ($n=1, 2, \ldots, 27$) are shown for the slice.

In a first approximation, first and second sequences of incremental ratios or derivative approximations $$(\Delta x/\Delta z)_n = (x_{n+1} - x_n)/(z_{n+1} - z_n) \qquad (1)$$

$$(\Delta y/\Delta z)_n = (y_{n+1} - y_n)/(z_{n+1} - z_n), \qquad (2)$$

are computed, using a linear approximation ratio for each of the derivatives. The first sequence of derivatives $\{(\Delta x/\Delta z)_n\}_n$ is then sub-divided into a group of one or more mutually exclusive sub-sequences $\{(\Delta x/\Delta z)_{nk}\}_k$ ($k=1, \ldots, K$), with each sub-sequence having a consecutive subset of the ratios $(\Delta x/\Delta z)_n$ with monotonically increasing, or monotonically decreasing, numerical values for the derivatives. In a similar manner, the second sequence of derivatives $\{(\Delta y/\Delta z)_m\}_m$ is then sub-divided into a group of one or more mutually exclusive sub-sequences $\{(\Delta y/\Delta z)_{mj}\}_j$ ($j=1, \ldots, J$), with each sub-sequence having a consecutive subset of the ratios $(\Delta y/\Delta z)_m$ with monotonically increasing, or monotonically decreasing, numerical values for the derivatives. Within each of the regions where the derivatives are monotonic, a simplified approximation to the local surface can be used.

The preceding equations are used to define regions of mating along the femoral anatomical axis. A change in slope from monotonic increase to decrease, or from monotonic decrease to increase, indicates that mating is no longer possible with respect to the FAA.

Figure 11:
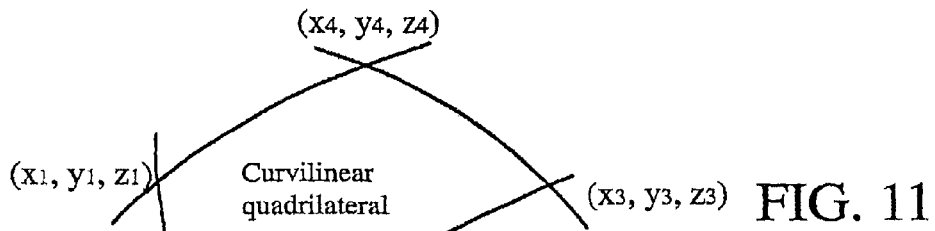

(1) Point-to-point bone surface mapping. Consider a quadrilateral Q(1,2,3,4), having a non-zero enclosed area and defined by four adjacent but distinct points, having coordinates $(x_n, y_n, z_n)$ ($n=1, 2, 3, 4$), as illustrated in FIG. 11, that are determined, using a CT scan, to lie on a surface BS of the bone 151 in FIGS. 10A and 10B. One goal is to determine a shape function $z = f_s(x,y)$ that is differentiable within a polygonal region and that satisfies $z_n = f_s(x_n, y_n)$ for $n=1, 2, 3, 4$. Consider first a situation in which no two or more x-coordinate values $x_n$ are equal and no two or more y-coordinate values $y_n$ are equal, referred to as a (4,4) situation, indicating that four distinct x-coordinates values and four distinct y-coordinate values are needed to define the quadrilateral Q(1,2,3,4). In this (4,4) situation, one suitable shape function for a quadrilateral grid is $$\begin{aligned}
z = {} & f_s(x, y; 4; 4; qu) \\
= {} & z_1(x-x_2)(x-x_3)(x-x_4)(y-y_2)(y-y_3)(y-y_4)/ \\
& (d_x(1; 2, 3, 4) \cdot d_y(1; 2, 3, 4)) + \\
& z_2(x-x_1)(x-x_3)(x-x_4)(y-y_1)(y-y_3)(y-y_4)/ \\
& (d_x(2; 1, 3) \cdot d_y(2; 1, 3, 4) + \\
& z_3(x-x_1)(x-x_2)(x-x_4)(y-y_1)(y-y_2)(y-y_4)/ \\
& (d_x(3; 1, 2, 4) \cdot d_y(3; 1, 2, 4)) + \\
& z_4(x-x_1)(x-x_2)(x-x_3)(y-y_1)(y-y_2)(y-y_3)/ \\
& (d_x(4; 1, 2, 3) \cdot d_y(4; 1, 2, 3)),
\end{aligned} \qquad (3)$$

$$d_x(a; b, c, d) = (x_a - x_b) \cdot (x_a - x_c) \cdot (x_a - x_d), \qquad (4)$$

$$d_y(a; b, c, d) = (y_a - y_b) \cdot (y_a - y_c) \cdot (y_a - y_d). \qquad (5)$$

At each of the four locations $(x_n, y_n, z_n)$, three of the four terms in the expression for $z = f_s(x, y; 4; 4; qu)$ vanish, and $f_s(x_n, y_n; 4; 4; qu) = z_n$.

In a (3,4) situation, only three of the four x-coordinate values are different (e.g., $x3 \neq x1 = x2 \neq x4 \neq x3$), but all four of the y-coordinate values are different from each other. In this (3,4) situation, the shape function is defined to be $$\begin{aligned}
z = {} & f_s(x, y; 3; 4; qu) \\
= {} & z_1(x-x_3)(x-x_4)(y-y_2)(y-y_3)(y-y_4)/ \\
& (d_x(1; 3, 4) \cdot d_y(1; 2, 3, 4)) + \\
& z_2(x-x_3)(x-x_4)(y-y_1)(y-y_3)(y-y_4)/ \\
& (d_x(2; 3, 4) \cdot d_y(2; 1, 3, 4)) + \\
& z_3(x-x_1)(x-x_4)(y-y_1)(y-y_2)(y-y_4)/ \\
& (d_x(3; 1, 4) \cdot d_y(3; 1, 2, 4)) + \\
& z_4(x-x_1)(x-x_3)(y-y_1)(y-y_2)(y-y_3)/ \\
& (d_x(4; 1, 3) \cdot d_y(4; 1, 2, 3)),
\end{aligned} \qquad (6)$$

-continued $$d_x(a; b, c) = (x_a - x_b) \cdot (x_a - x_c), \quad (7)$$

$$d_y(a; b, c) = (y_a - y_b) \cdot (y_a - y_c). \quad (8)$$

For the (4,3) situation, with four distinct x-coordinates values and only three distinct y-coordinate values, the shape function $z=f_s(x,y,4;3;qu)$ is defined analogous to the shape function $z=f_s(x,y;3;4,qu)$ in Eq. (6).

In a (2,4) situation, only two of the four x-coordinate values are different (e.g., x1=x2≠x3=x4), but all four of the y-coordinate values are different from each other. In this (2,4) situation, the shape function is defined to be $$\begin{aligned} z &= f_s(x, y; 2; 4; qu) \quad (9) \\ &= z_1(x - x_3)(y - y_2)(y - y_3)(y - y_4) / \\ & \quad (d_x(1; 3) \cdot d_y(1; 2, 3, 4)) + \\ & \quad z_2(x - x_3)(y - y_1)(y - y_3)(y - y_4) / \\ & \quad (d_x(2; 3) \cdot d_y(2; 1, 3, 4)) + \\ & \quad z_3(x - x_1)(y - y_1)(y - y_2)(y - y_4) / \\ & \quad (d_x(3; 1) \cdot d_y(3; 1, 2, 4)) + \\ & \quad z_4(x - x_1)(y - y_1)(y - y_2)(y - y_3) / \\ & \quad (d_x(4; 1) \cdot d_y(4; 1, 2, 3)), \end{aligned}$$

$$d_x(a; b) = (x_a - x_b), \quad (10)$$

$$d_y(a; b) = (y_a - y_b). \quad (11)$$

For the (4,2) situation, with four distinct x-coordinates values and only two distinct y-coordinate values, the shape function $z=f_s(x,y;4;2;qu)$ is defined analogous to the shape function $z=f_s(x,y;2;4;qu)$ in Eq. (9).

In a (3,3) situation, only three of the x-coordinate values are different (e.g., x3≠x1=x2≠x4≠x3), and only three of the y-coordinate values are different (e.g., y4≠y1=y2=y3≠y4). In this (3,3) situation, the shape function is defined to be $$\begin{aligned} z &= f_s(x, y; 3; 3; qu) \quad (12) \\ &= z_1(x - x_3)(x - x_4)(y - y_2)(y - y_4) / \\ & \quad (d_x(1; 3, 4) \cdot d_y(1; 2, 4)) + \\ & \quad z_2(x - x_3)(x - x_4)(y - y_1)(y - y_4) / \\ & \quad (d_x(2; 3, 4) \cdot d_y(2; 1, 4)) + \\ & \quad z_3(x - x_1)(x - x_4)(y - y_1)(y - y_4) / \\ & \quad (d_x(3; 1, 4) \cdot d_y(3; 1, 4)) + \\ & \quad z_4(x - x_1)(x - x_3)(y - y_1)(y - y_2) / \\ & \quad (d_x(4; 1, 3) \cdot d_y(4; 1, 2)), \end{aligned}$$

In a (2,3) situation, two of the four x-coordinate values are different (e.g., x1=x2≠x3=x4), and three of the y-coordinate values are different to from each other (e.g., y1≠y2=y3≠y4≠y3). In this (2,4) situation, the shape function is defined to be $$\begin{aligned} z &= f_s(x, y; 2; 3; qu) \quad (13) \\ &= z_1(x - x_3)(y - y_2)(y - y_4) / \end{aligned}$$

$$(d_x(1; 3) \cdot d_y(1; 2, 4)) +$$
$$z_2(x - x_3)(y - y_1)(y - y_4) /$$
$$(d_x(2; 3) \cdot d_y(2; 2, 4)) +$$
$$z_3(x - x_1)(y - y_1)(y - y_4) /$$
$$(d_x(3; 1) \cdot d_y(3; 1, 4)) +$$
$$z_4(x - x_1)(y - y_1)(y - y_2) /$$
$$(d_x(4; 1) \cdot d_y(4; 1, 2)),$$

For the (3,2) situation, with three distinct x-coordinates values and two distinct y-coordinate values, the shape function $z=f_s(x,y,3,2;qu)$ is defined analogous to the shape function $z=f_s(x,y2;3;qu)$ in Eq. (13).

In a (2,2) situation, two of the four x-coordinate values are different (e.g., x1=x2≠x3=x4), and two of the y-coordinate values are different (e.g., y4=y1≠y2=y3). In this (2,2) situation, the shape function is defined to be $$\begin{aligned} z &= f_s(x, y; 2; 2; qu) \quad (14) \\ &= z_1(x - x_3)(y - y_2)/(d_x(1; 3) \cdot d_y(1; 2)) + \\ & \quad z_2(x - x_3)(y - y_1)/(d_x(2; 3) \cdot d_y(2; 1)) + \\ & \quad z_3(x - x_1)(y - y_1)/(d_x(3; 1) \cdot d_y(3; 1)) + \\ & \quad z_4(x - x_1)(y - y_2)/(d_x(4; 1) \cdot d_y(4; 2,)), \end{aligned}$$

Figure 12:
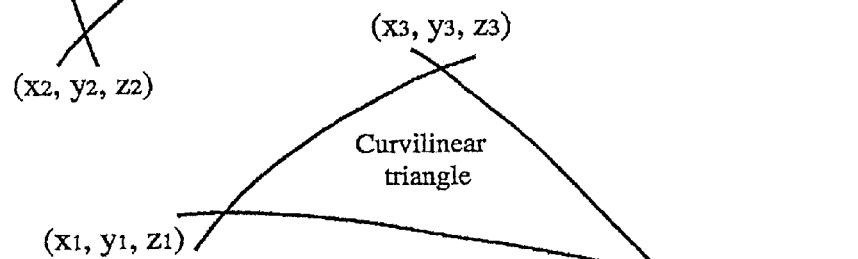

More generally, the quadrilateral Q(1,2,3,4) can be replaced by an M-vertex polygon (M≥3) having non-zero included numerical area, and a shape function for this polygon is determined by analogy to the preceding development. The simplest polygon here, having the lowest corresponding polynomial degree in x and y, is a triangle (M=3). The particular shape function used will depend upon the configuration of the polygon relative to the coordinate axes. For definiteness, it may be assumed here that the bone surface BS is divided by a grid of quadrilaterals (or triangles) and that the coordinate values $(x_n, y_n, z_n)$ (n=1, 2, 3, 4) of the vertices are known from analysis of the CT scan.

Where a sequence of triangles, rather than a sequence of quadrilaterals, is used to define a grid for the bone surface, as illustrated in FIG. 12, three coordinate triples $(x_n, y_n, z_n)$ (n=1, 2, 3) are provided to define each such triangle. In a (3,3) situation, all three of the x-coordinate values are different (x3≠x1≠x2≠x3), and all three of the y-coordinate values are different (y3≠y1≠y2≠y3). In this (3,3) situation, the shape function for a triangular grid is defined to be $$\begin{aligned} z &= f_s(x, y; 3; 3; tr) \quad (15) \\ &= z_1(x - x_2)(x - x_3)(y - y_2)(y - y_3) / \\ & \quad (d_x(1; 2, 3) \cdot d_y(1; 2, 3)) + \\ & \quad z_2(x - x_1)(x - x_3)(y - y_1)(y - y_3) / \\ & \quad (d_x(2; 1, 3) \cdot d_y(2; 1, 3)) + \end{aligned}$$

$$z_3(x-x_1)(x-x_2)(y-y_1)(y-y_2)/$$
$$(d_x(3;1,2) \cdot d_y(3;1,2)).$$

In a (2,3) situation, where only two x-coordinate values are different (e.g., x1=x2≠x3) and all three y-coordinate values are different, the shape function is defined to be $$z = f_s(x, y; 2; 3; tr) \quad (16)$$
$$= z_1(x-x_3)(y-y_2)(y-y_3)/$$
$$(d_x(1;3) \cdot d_y(1;2,3)) +$$
$$z_2(x-x_3)(y-y_1)(y-y_3)/$$
$$(d_x(2;3) \cdot d_y(2;1,3)) +$$
$$z_3(x-x_1)(y-y_1)(y-y_2)/$$
$$(d_x(3;1) \cdot d_y(3;1,2)).$$

For the (3,2) situation, with three distinct x-coordinates values and two distinct y-coordinate values, the shape function $z=f_s(x,y;3;2;tr)$ is defined analogous to the shape function $z=f_s(x,y;2;3;tr)$ in Eq. (16).

In a (2,2) situation, two of the three x-coordinate values are different (e.g., x1=x2≠x3), and two of the three y-coordinate values are different (e.g., y1≠y2=y3). In this (2,2) situation, the shape function is defined to be $$z = f_s(x, y; 2; 2; tr) \quad (17)$$
$$= z_1(x-x_3)(y-y_2)(y-y_3)/$$
$$(d_x(1;3) \cdot d_y(1;2)) +$$
$$z_2(x-x_3)(y-y_1)/$$
$$(d_x(2;3) \cdot d_y(2;1)) +$$
$$z_3(x-x_1)(y-y_1)/$$
$$(d_x(3;1) \cdot d_y(3;1)).$$

Where a quadrilateral grid is used and, for a given quadrilateral, precisely M x-coordinate values are different and precisely N y-coordinate values are different (2≤M≤4; 2≤N≤4), the shape function is a polynomial of degree M−1 in x and of degree N−1 in y. Utilizing the theory of equations and roots of equations, one can show that the shape function defined in this manner for a quadrilateral, satisfying $f_s(x_n,y_n;M;N;qu)=z_n$ (n=1, 2, 3, 4) and having minimal polynomial degree, is unique, although the polynomial itself may be expressed in different, equivalent ways.

Where a triangular grid is used and, for a given triangular, precisely M x-coordinate values are different and precisely N y-coordinate values are different (2≤M≤3; 2≤N≤3), the shape function is a polynomial of degree M−1 in x and of degree N−1 in y. Utilizing the theory of equations and roots of equations, one can show that the shape function defined in this manner for a quadrilateral, satisfying $f_s(x_n,y_n;M;N;tr)=z_n$ (n=1, 2, 3) and having minimal polynomial degree, is unique, although the polynomial itself may be expressed in different, equivalent ways. The shape function polynomial for a triangular grid has smaller polynomial degree in x and in y (as small as degree 1 in each of x and in y) than the corresponding shape function polynomial for a quadrilateral grid.

The shape function, $f_s(x,y;M;N;tr)$ or $f_s(x,y;N;qu)$, may be used as is to describe a minimal polynomial surface for a particular polygon satisfying $f_s(x_n,y_n;M;N;tr$ or $qu)=z_n$. If desired, the grid adopted may include a mixture of triangles and quadrilaterals, with each such polygon having its own shape function. That is, if the grid includes a total of K polygons (e.g., triangles and/or quadrilaterals), a total of K shape functions are defined, using the preceding mathematical construction.

(2) Bone surface normal mapping. The components of a vector n(x,y) normal to the bone surface defined by the shape function for a particular quadrilateral are determined to be $$n(x,y)=\{\partial f_s/\partial x, \partial f_s/\partial y, -1\}, \quad (18)$$

where the vector components can be, but need not be, normalized to unit length, if desired. These normal vector components can be used to determine the local surface normal n(x,y) for an implant device that approximates as closely as possible the bone surface BS imaged by the CT scan. Again, if the grid includes a total of K polygons (e.g., triangles and/or quadrilaterals), a total of up to K shape functions are defined, using the preceding mathematical construction, and a surface normal at a selected location within each polygon is computed.

Figure 13:
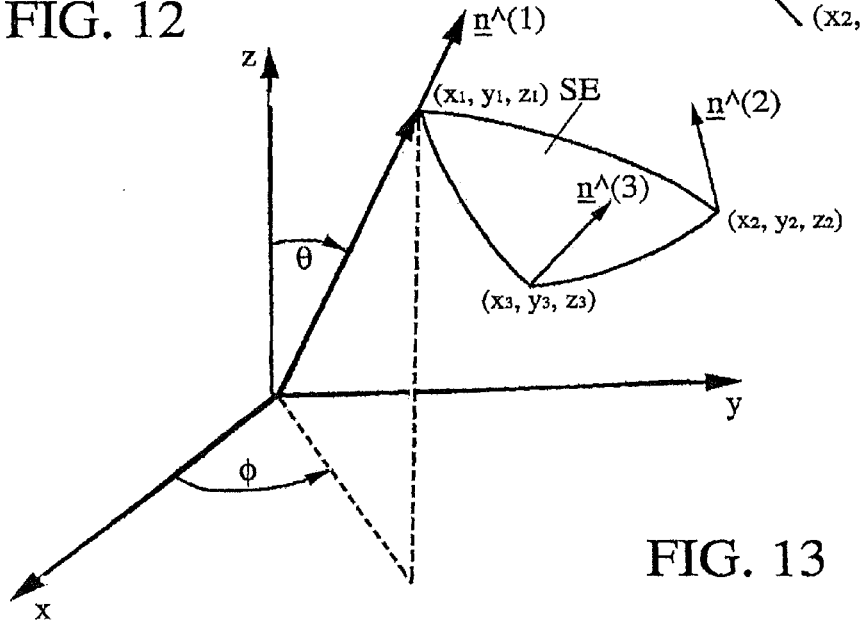
FIG. 13 illustrates a procedure for estimating a local surface for surface normal vector matching.

FIG. 13 illustrates a surface element SE, defined by three spaced apart locations with Cartesian coordinates $(x_m, y_m, z_m)$ (m=1, 2, 3), with each location having a surface normal of unit length n^(m) that is specified, for example, by information from the CT image. With reference to a spherical coordinate system (r,θ,φ) that is aligned as shown with the Cartesian coordinate system, the vector components of a unit-length normal at a given location are expressible as $$n\hat{}=(\cos\phi\cdot\sin\theta, \sin\phi\cdot\sin\theta, \cos\theta). \quad (19)$$

A local surface element defined by the three locations $(x_m, y_m, z_m)$ is approximated by a surface element of an ellipsoid that is rotated by an angle ψ in the (x,y)-plane relative to the x-coordinate axis $$\{(x-x0)\cos\psi+(y-y0)\sin\psi\}^2/a^2+\{-(x-x0)\sin\psi+(y-y0)\cos\psi\}^2/b^2+(z-z0)^2/c^2=1, \quad (20)$$

where a, b and c are three positive numbers and x0, y0 and z0 are three coordinate values, and ψ is a rotation angle, as yet unspecified. Locally, the ellipsoid surface can be re-expressed in functional form as $$z(x,y)=z0\pm c\{1-u^2-v^2\}^{1/2}, \quad (21)$$
$$\partial z/\partial x=-(\pm)(c/a)u/\{1-u^2-v^2\}^{1/2}, \quad (22)$$
$$\partial z/\partial y=-(\pm)(c/b)v/\{1-u^2-v^2\}^{1/2}, \quad (23)$$
$$u=\{(x-x0)\cos\psi+(y-y0)\sin\psi\}/a, \quad (24)$$
$$v=\{-(x-x0)\sin\psi+(y-y0)\cos\psi\}/b. \quad (25)$$

The expressions for ∂z/∂x and ∂z/∂y are strictly monotonic (increasing or decreasing) in each of the variables u and v and range from −∞ to +∞ so that, for any pair of real numbers (w1,w2), unique values u and v can be found for Eqs. (22) and (23) for which ∂z/∂x=w1 and ∂z/∂y=w2. Vector components for a unit-length normal vector for the surface z(x,y) are expressible as $$n\hat{}=(\pm(c/a)u,\pm(c/b)v,-\{1-(c/a)^2u^2-(c/b)^2v^2\}^{1/2}), \quad (26)$$

and unit-length surface normal vectors n^(m) are to be matched at three locations, $(x,y,z)=(x_m,y_m,z_m)$. Matching of the third of these three vector components is automatic (apart from the signum) for a unit-length vector. These vector components matching requirements are expressed as $$(c/a)u_m = c \cdot \{(x_m-x0)\cos\psi + (y_m-y0)\sin\psi\}/a^2 = \cos\phi_m \cdot \sin\theta_m, \quad (27A)$$

$$(c/b)v_m = c \cdot \{-(x_m-x0)\sin\psi + (y_m-y0)\cos\psi\}/b^2 = \sin\phi_m \cdot \sin\theta_m, \quad (27B)$$

(m=1, 2, 3), where the right hand expressions are specified or measured values. Equations (27A) and (27B) can also be rotated and thereby expressed in the form $$x_m - x0 = (a^2/c)\cos\psi\cos\phi_m\sin\theta_m - (b^2/c)\sin\psi\sin\phi_m\sin\theta_m, \quad (28A)$$

$$y_m - y0 = (a^2/c)\sin\psi\cos\phi_m\sin\theta_m + (b^2/c)\cos\psi\sin\phi_m\sin\theta_m, \quad (28B)$$

Equations (27A) and (27B), or (28A) and (28B), are six equations in six explicit unknowns (x0, y0, $\psi$, a, b, c), and solutions can be found. Each surface element may have a different set of these unknowns, but two adjacent surface elements with a common vertex will have the same surface normal at that common vertex.

Once these six unknowns are determined, the ellipsoidal surface element extending between the three locations or vertices $(x_m, y_m, z_m)$ is defined, with a surface normal that varies continuously from a surface normal at one of these vertices to a surface normal at another of these vertices. These surface elements become part of a surface mosaic that provides a well defined surface normal within the surface element interior. No matter which direction a surface element vertex is approached, from within any surface element that has that vertex, the surface normal vector will approach the same normal vector associated with that vertex. Although an ellipsoid, defined in Eq. (20) has been used here, any other three-dimensional conic, such as a saddle surface with at least one + sign replaced by a − sign in Eq. (20), can be used for surface normal matching in appropriate circumstances.

(3) Bone surface-to-surface mapping. A surface-to-surface mapping is an extension of bone surface normal mapping, using a significantly larger number of data points and surface normal vectors within selected regions.

Construction of a mathematical model of a portion of a bone surface has used polynomials in a Cartesian coordinate set (x,y,z). One could, as well, use a multi-coordinate Fourier series, expressed in cylindrical coordinates (r($\theta$,z),$\theta$, z) or in another suitable coordinate set, for the location of selected points on a bone surface.

Any other suitable approach for point-to-point mapping and/or surface normal mapping can be used here to determine or estimate a mathematically expressed surface for a selected portion of a bone.

Although the example herein has focused on TJA for a patient's knee, the procedure is applicable to any other joint as well, such as a patient's hip, foot, toe, elbow, shoulder, wrist, finger or neck joint.

The invention claimed is:

1. A method of manufacturing a custom arthroplasty jig for use in an arthroplasty procedure on a damaged bone of a patient, the method comprising:
   obtaining a medical image of a selected region of the damaged bone of the patient;
   using a computer processor to analyze the medical image to provide at least first, second and third location coordinate values for each of a selected sequence of surface point locations on the selected region of the damaged bone, the surface point locations corresponding to a surface shape of the selected region;
   using the computer processor to construct a bone surface computer model including the surface shape of the selected region of the damaged bone by: selecting a sequence of one or more polygons defined by the sequence of surface point locations, the polygons defining the surface shape of the selected region in the bone surface computer model; and performing at least one of a point-to-point mapping or a surface normal vector mapping to construct the bone surface computer model; and
   using the bone surface computer model to generate, via the computer processor, computer-readable automated instructions for a production machine to fabricate, before any incision in the patient, the custom arthroplasty jig configured for cutting and removing at least a portion of the selected region of the damaged bone, the custom arthroplasty jig including a patient specific mating surface that matches the surface shape of the selected region in the bone surface computer model such that the custom arthroplasty jig is capable of mating with the selected region of the damaged bone in only a single orientation during the arthroplasty procedure,
   wherein the custom arthroplasty jig is configured such that, when the surface shape of the selected region of the damaged bone is matingly received in the patient specific mating surface, cutting the damaged bone with a cutting instrument guided by the custom arthroplasty jig provides at least one selected planar surface in the damaged bone that has a preoperatively planned alignment with a selected axis of the damaged bone.

2. The method of claim 1, wherein said process of constructing said bone surface computer model of said damaged bone comprises: for at least one polygon in said sequence of said polygons, determining a number V of vertices of the at least one polygon; and providing a polynomial z=f(x,y) of degree at most V−1 in said first location coordinate x and of degree at most V−1 in said second location coordinate y, defined on the at least one polygon, where the polynomial has a value equal to a selected value of z at each of the V vertices of the at least one polygon.

3. The method of claim 2, further comprising selecting said polynomial f(x,y) to have a minimum polynomial degree in said coordinate x and to have a minimum polynomial degree in said coordinate y.

4. The method of claim 2, further comprising selecting each of said selected values z to correspond to said third location coordinate value for each of said vertices of said at least one polygon.

5. The method of claim 2, further comprising choosing said at least one polygon to be a triangle with non-zero included area.

6. The method of claim 2, further comprising choosing said at least one polygon to be a quadrilateral with non-zero included area.

7. The method of claim 1, wherein said process of constructing said bone surface computer model of said damaged bone comprises: providing component values of a surface normal vector at each of at least three vertex locations of a selected surface element on the selected region of the damaged bone; providing a surface element defined by a selected polynomial of second degree in at least two of three Cartesian location coordinates (x,y,z), the polynomial having at least six initially undetermined parameters; and determining values for the undetermined parameters so that a surface normal vector of the surface element has the provided surface normal vector component values at each of the at least three vertex locations.

8. The method of claim 7, further comprising selecting said polynomial to represent an ellipsoid in three dimensions.

9. The method of claim 1, further comprising choosing a joint associated with said damaged bone from a group of joints consisting of a hip joint, a knee joint, a foot joint, a toe joint, a shoulder joint, an elbow joint, a wrist joint, a finger joint and a neck joint.

10. The method of claim 1, wherein the selected axis of the damaged bone is a femoral mechanical axis.

11. The method of claim 10, wherein the femoral mechanical axis extends through a center of the femoral head and a center of the knee.

12. The method of claim 11, wherein the preoperatively planned alignment of the at least one selected planar surface is perpendicular to the femoral mechanical axis.

13. The method of claim 12, wherein information relating to the at least one selected planar surface is used to define a resection guide surface in the custom arthroplasty jig, the resection guide surface configured to guide the cutting instrument in cutting the damaged bone to provide the at least one selected planar surface.

14. The method of claim 1, wherein the custom arthroplasty jig further comprises a resection guide surface that is configured to guide the cutting instrument in cutting the damaged bone.

15. The method of claim 1, wherein the custom arthroplasty jig further comprises:
a first component that includes the patient specific mating surface; and
a second component that is removeably coupled to the first component of the custom arthroplasty jig,
wherein the second component includes at least a first portion of a resection guide surface that is configured to guide the cutting instrument in cutting the damaged bone.

16. The method of claim 15, wherein the first component further includes at least a second portion of a resection guide surface that is configured to guide the cutting instrument in cutting the damaged bone.

17. The method of claim 1, wherein the medical image comprises a CT image or an MRI image.

18. A method of manufacturing a custom arthroplasty jig for use in an arthroplasty procedure on a damaged femur bone of a patient, the method comprising:
obtaining a medical image of a selected region of the damaged femur bone;
using a computer processor to analyze the medical image to provide at least first, second and third location coordinate values for each of a selected sequence of surface point locations on the damaged femur bone;
using the computer processor to generate a computer bone model of a selected portion of a surface of the selected region of the damaged femur bone by implementing at least one of a point-to-point mapping or a surface normal vector mapping for each of a selected sequence of one or more polygons defined by the sequence of surface point locations;
using the computer bone model in generating computer readable automated instructions for a fabrication machine, the automated instructions configured to instruct the fabrication machine to fabricate, before any incision in the patient, the custom arthroplasty jig for use in cutting and removing at least a part of the selected portion during the arthroplasty procedure; and
fabricating with the fabrication machine the custom arthroplasty jig having a patient specific mating surface and a cutting guide, the fabrication machine utilizing the automated instructions,
wherein the patient specific mating surface substantially matches at least a portion of a surface of the computer bone model and is configured to matingly receive the selected portion of the selected region of the damaged femur bone such that the custom arthroplasty jig is capable of mating with the selected portion of the selected region of the damage femur bone in only a single orientation, and further wherein the cutting guide is configured to guide a cutting instrument in cutting the selected portion of the selected region of the damaged femur bone during the arthroplasty procedure to create a planar resection in the damaged femur bone that is perpendicular to a femoral mechanical axis of the femur bone.

19. The method of claim 18, wherein the femoral mechanical axis extends through a center of the femoral head and a center of the knee.

20. The method of claim 18, wherein the medical image comprises a CT image or a MRI image.

21. The method of claim 18, wherein said process of generating said computer bone model of the selected portion of the selected region of said damaged femur bone comprises: for at least one polygon in said sequence of said polygons, determining a number V of vertices of the at least one polygon; and providing a polynomial $z=f(x,y)$ of degree at most $V-1$ in said first location coordinate x and of degree at most $V-1$ in said second location coordinate y, defined on the at least one polygon, where the polynomial has a value equal to a selected value of z at each of the V vertices of the at least one polygon.

22. The method of claim 21, further comprising selecting said polynomial $f(x,y)$ to have a minimum polynomial degree in said coordinate x and to have a minimum polynomial degree in said coordinate y.

23. The method of claim 21, further comprising selecting each of said selected values z to correspond to said third location coordinate value for each of said vertices of said at least one polygon.

24. The method of claim 21, further comprising choosing said at least one polygon to be a triangle with non-zero included area.

25. The method of claim 21, further comprising choosing said at least one polygon to be a quadrilateral with non-zero included area.

* * * * *

UNITED STATES PATENT AND TRADEMARK OFFICE
CERTIFICATE OF CORRECTION

| | |
|---|---|
| PATENT NO. | : 8,801,719 B2 |
| APPLICATION NO. | : 13/730585 |
| DATED | : August 12, 2014 |
| INVENTOR(S) | : Park et al. |

Page 1 of 1

It is certified that error appears in the above-identified patent and that said Letters Patent is hereby corrected as shown below:

In the Claims

Column 20, line 9, replace "iig" with -- jig --.

Signed and Sealed this
Sixteenth Day of December, 2014

Michelle K. Lee
*Deputy Director of the United States Patent and Trademark Office*